United States Patent
Valle et al.

(10) Patent No.: US 6,407,072 B1
(45) Date of Patent: *Jun. 18, 2002

(54) LYSOGANGLIOSIDE DERIVATIVES

(75) Inventors: Francesco Della Valle, Padua; Aurelio Romeo, Rome, both of (IT)

(73) Assignee: Fidia S.p.A., Abano Terme (IT)

( * ) Notice: Subject to any disclaimer, the term of this patent is extended or adjusted under 35 U.S.C. 154(b) by 0 days.

This patent is subject to a terminal disclaimer.

(21) Appl. No.: 08/268,730

(22) Filed: Jun. 30, 1994

Related U.S. Application Data

(63) Continuation of application No. 07/443,657, filed on Nov. 30, 1989, now abandoned.

(30) Foreign Application Priority Data

Dec. 2, 1988 (IT) .......................................... 48618A/88

(51) Int. Cl.$^7$ .............................................. A61K 31/70
(52) U.S. Cl. ............................ 514/25; 514/54; 536/4.1; 536/53; 536/55.1; 536/122
(58) Field of Search ........................ 514/25, 54; 536/53, 536/55.1, 4.1, 122

(56) References Cited

U.S. PATENT DOCUMENTS

| | | | | |
|---|---|---|---|---|
| 4,308,254 A | * | 12/1981 | Tayot et al. | 436/529 |
| 4,347,244 A | * | 8/1982 | Mynard et al | 514/25 |
| 4,415,733 A | * | 11/1983 | Tayot et al. | 536/53 |
| 4,476,119 A | | 10/1984 | della Valle et al. | 536/53 |
| 4,593,091 A | * | 6/1986 | Della Valle et al. | 536/55.1 |
| 4,713,374 A | * | 12/1987 | Della Valle et al. | 536/55.1 |
| 4,716,223 A | | 12/1987 | della Valle et al. | 536/53 |
| 4,859,769 A | * | 8/1989 | Karlsson et al. | 536/53 |
| 5,264,424 A | * | 11/1993 | Della Valle et al. | 514/54 |
| 5,281,702 A | * | 1/1994 | Tubaro et al. | 536/53 |
| 5,330,977 A | * | 7/1994 | Tubaro et al. | 574/53 |
| 5,350,841 A | * | 9/1994 | Romeo et al. | 536/53 |

FOREIGN PATENT DOCUMENTS

| | | |
|---|---|---|
| EP | 0072722 | 2/1983 |
| EP | 0352766 | 1/1990 |
| WO | 8603971 | 7/1986 |

OTHER PUBLICATIONS

Methods in Enzymol; vol. 138, 319–349, Schwazzmaan (1987).*
Febs Lett. 185(1) 112:114, Neuenhofer (1985).*
Annu. Rev. Pharamcol. Toxicol—30:40–71 (1990) Olney.*
Neuenhofer et al; FEBS Lett. 185(1):112–114 (1985).*
Fishman et al.; J. Biol. Chem. 255 (16):7657–7664 (1980).*
Handa et al.; Adv. Exp. Med. Biol. 152:23–31 (1982).*
Sonnino et al.; J. Lipid Res. 26:248–257 (1985).*
Neuenhofer et al; Biochem. 24:525–532 (1985).*
The Merck Manual; 15$^{th}$ Ed. pp. 1326–1395 and 1433–1453 (1987).*
Schwarzmann et al; Meth. Enz. 138:319–341 (1987).*
Hanai et al; Biochem. Biophys. Res. Comm. 147(1):127–134 (Aug. 31, 1987).*
Hirabayashi et al; J. Biochem. 103(1):1–4 (1988).*
Hanai et al; J. Biol. Chem. 263(22):10915–10921 (1988).*
Nores et al; Carb. Res. 179:393–410 (1988).*
Masserini et al; Biochem. 28:5029–5034 (1989).*
Schwarzmann et al, Methods in Enzymology, vol. 138 (1987) pp 319–341.
Ledeen et al, Glycolipid Methodology, Lloyd A. Witting Ed., (1976) pp. 187–214.
Brunngraber et al. Glycolipid Methodology, Lloyd A. Witting Ed., (1976) pp. 159–186.
Miceli et al, Acta Psychiat. Scand., vol. 55, (1977) pp. 102–110.
Grillo, Europa Medicophysica, vol. 13, (1977) pp. 1–8.
Ceccarelli et al, Adv. Exp. Med. Biol., vol. 71, (1976) pp. 275–293.
Mingione et al, Electromyogr. clin. Neurophysiol., vol. 19, (1979) pp. 353–359.
Viva et al, Minerva Stomat., vol. 27, (1978) pp. 177–184.
Negrin et al, Minerva Medica, vol. 69 (1978) pp. 3277–3282.
Aporti et al, Med. del Lavoro, vol. 68, (1977) pp. 296–302.
Gorio et al, Brain Research, vol. 197, (1980) pp. 236–241.
Leon et al, Journal of Neurochemistry, vol. 37, (1981) pp. 350–357.
Svennerholm, Journal of Neurochemistry, vol. 10, (1963) pp. 613–623.
Vaccarino et al, Proc. Natl. Acad. Sci. USA, vol. 84 (1987) pp. 8707–8711.
Hannun et al, Journal of Biological Chemistry, vol. 261, (1986) pp. 12604–12609.
Merrill et al, Journal of Biological Chemistry, vol. 261, (1986) pp. 12610–12615.
Wilson et al, Journal of Biological Chemistry, vol. 261, (1986) pp. 12616–12623.
Hannun et al., Science, vol. 235, (1987) pp. 670–673.
Gallo et al, Proc. Natl. Acad. Sci. USA, vol. 79, (1982) pp. 7919–7923.
Vaccarino et al, Journal of Neuroscience, vol. 7, (1987) pp. 65–76.

(List continued on next page.)

Primary Examiner—Kathleen K. Fonda
(74) Attorney, Agent, or Firm—Birch, Stewart, Kolasch & Birch, LLP

(57) ABSTRACT

Novel N-acyl-lysogangliosides obtained from gangliosides by deacyation of the ceramide group, wherein the acyl group is derived from an aliphatic acid having from 2 to 24 carbon atoms, substituted by one or more polar groups. The N-acyl-lysogangliosides of the invention exhibit an inhibiting action on protein-kinase C activation and, thus, can be utilized in therapies for various pathologies of the nervous system.

3 Claims, 7 Drawing Sheets

U.S. PATENT DOCUMENTS

Lowry et al, Journal of Biological Chemistry, vol. 193, (1951) pp. 256–275.

McDonald et al, European Journal of Pharmacology, vol. 140, (1987) pp. 359–361.

Andine et al, Neuroscience Letters, vol. 90, (1988) pp. 208–212.

Hirabayashi et al, Journal of Biochemistry, vol. 103 , (1988) pp. 1–4.

Neuenhofer et al, Biochemistry, vol. 24, (1985) pp. 525–532.

Fishman et al, Journal of Biological Chemistry, vol. 255, No. 16, (1980) pp. 7657–7664.

Biol. Chem. Hoppe Seyler, vol. 367, (1986) p. 241.

Nores et al, Carbohydrate Research, vol. 179, (1988) pp. 393–410.

Hanai et al, Biochemical and Biophysical Research Comm., vol. 147, No. 1 (1987) pp. 127–134.

Bouhours et al, Journal of Biological Chem., vol. 258, No. 1, (Jan. 10, 1983) pp. 299–304.

Bouhours et al, Biochimica et Biophysica Acta, vol. 487 (1977) pp. 51–60.

Cochran et al, Journal of Neurochemistry, vol. 36, No. 2 (1981) pp. 696–702.

Bouchon et al, Biochemistry International, vol. 10, No. 4 (Apr. 1985) pp. 531–538.

Kawano et al, CA 111:4544p (Jul. 1989).

Sonnino et al, Biochemistry, vol. 28, (1989) pp. 77–84.

Tiemeyer et al, Journal of Biological Chemistry, vol. 264, No. 3, (Jan. 1989) pp. 1671–1681.

Ladisch et al, Journal of Biological Chemistry, vol. 264, No. 20 (Jul. 1989) pp. 12097–12105.

Aangstroem et al, CA 96:176889d (1982) (Dep. Biochem. Univ. Goeteborg, Sweden.

Klenk et al, CA 68:9505e (1968) Hoppe Seyler's Z. Physiol. Chem. 348(10), 1967, 1261–7).

* cited by examiner

LYSOGANGLIOSIDE DERIVATIVES

This application is a continuation of application Ser. No. 07/443,657 filed on Nov. 30, 1989, now abandoned.

The present invention is directed to new lysoganglioside derivatives and more particularly to novel N-acyl lysogangliosides, in which the acyl group is derived from an aliphatic acid substituted by one or more polar groups.

Lysogangliosides are derivatives obtainable from gangliosides by deacylation of the ceramide group, which retain only the sphingosine residue. Gangliosides are generally mixtures of various unitary chemical compounds having the following formula:

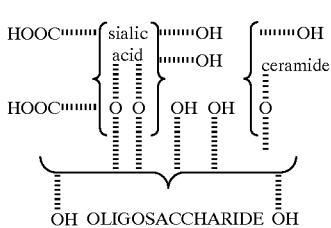
(I)

These molecules contain an oligosaccharide part, generally well defined chemically for each ganglioside, a sialic part (that is, constituted by one or more sialic acids) and a ceramide part, these last three parts being generally constituted by a mixture of different sialic acids and different ceramide residues.

Sialic acids are acyl derivatives of neuraminic acid of the formula

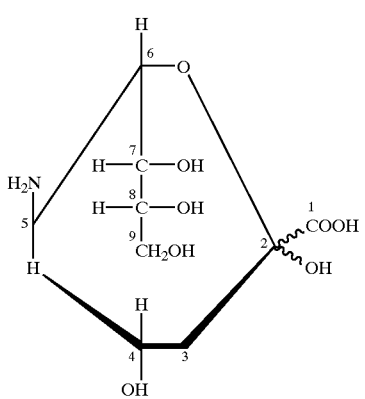
(II)

wherein the amino group is acylated with acetic or glycolic acid and the hydroxyl groups may also be esterified with such acids. The ceramide group represents an N-acylsphingosine corresponding to one of the two following formulae:

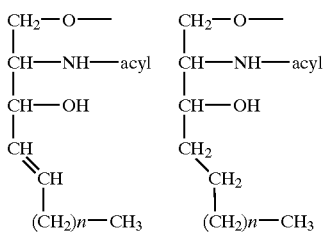

in which n is 6 to 18 and the acyl group is derived from a saturated or unsaturated fatty acid having from 16 to 22 carbon atoms or from a corresponding hydroxy acid. As noted above, in gangliosides the sialic and ceramide residues are mixtures of the groups having the above formulae, and this is true also for the purified gangliosides described in the literature. The number of sialic acids present in gangliosides usually varies between 1 and 5. The sialic residues are bound to the oligosaccharide by a ketosidic bond formed by the hydroxyl at the 2-position with a hydroxyl group in the oligosaccharide. When several sialic acids are bound together, the union between them is brought about by ketosidic bonds formed between the hydroxyl groups at the 2- and 8-positions of two sialic acid molecules. The sialic acids of gangliosides, and of those which are purified as previously described, are mixtures of various chemically unitary acids, for example, N-acetylneuraminic acid and N-glycolylneuraminic acid, in which the former is predominant, and possibly of one or more of their O-acylderivatives, for example, the 8-O-acylderivatives.

The oligosaccharide is composed of a maximum of 5 monosaccharides or derivatives thereof with an acylamino group, especially hexoses and their derivatives of the above-mentioned type. There is, however, always present in the oligosaccharide at least one glucose or galactose molecule, the most frequent residue as the acylamino derivative of the above-mentioned sugars being N-acetylglucosamine and N-acetylgalactosamine. Lysogangliosides, as defined above, can be obtained by enzymatic deacylation of the nitrogen on the ceramide. If deacylation is effected chemically, for example, by alkaline hydrolysis, other esterified acylamino or hydroxy groups are deacylated, such as, especially, the acyl present on the nitrogen of the neuraminic or acyl acids possibly present, (usually to a lesser degree) on the hydroxy groups of such acids.

As has been noted above, the acyl groups present in gangliosides on the nitrogen of the neuraminic acid are derived from acetic acid and possibly, to a far lesser degree, from glycolic acid. Selective reacylation, for example, after temporarily protecting the sphingosine amino group, gives products of the type of lysogangliosides obtained by enzymatic deacylation, which differ therefrom only in the exclusive presence of the acetyl group on the neuraminic nitrogen and possibly in the absence of acylating groups on the hydroxyl groups of this acid. This group of deacylated derivatives also serves as a substrate for the preparation of new N-acyl lysogangliosides, and the term "lysogangliosides" is used in the present application to mean both the products of enzymatic deacylation and products obtained in the above-said manner by chemical deacylation.

The compounds of the present invention are semisynthetic analogues of gangliosides and differ therefrom due to the presence of a single well-defined N-acyl group in the sphingosine part and with acids which are very different from those of natural products. They are new, even though among natural gangliosides, products have been found which, when hydrolyzed, give rise to the formation of higher aliphatic acids substituted by hydroxy groups (and therefore polar groups, such as those of the present invention). However, the corresponding products have never been isolated and have never been described. The invention also includes functional derivatives of the sialic carboxy groups of the new N-acyl lysogangliosides, that is, esters and amides, and also inner esters having lactone bonds among the sialic carboxy groups and hydroxyl groups of the oligosaccharide, analogues and known derivatives of gangliosides, as well as peracylated derivatives of the hydroxyl groups of the ganglioside, both of N-acyl lysogangliosides themselves and of their functional derivatives as mentioned above.

The main object of the present invention is directed to N-acyl lysogangliosides, in which the acyl group is derived from an aliphatic acid having from 2 to 24 carbon atoms, substituted by one or more polar groups chosen from the following group:

chlorine, bromine and fluorine;

free hydroxy groups or hydroxy groups esterified with an organic or inorganic acid;

etherified hydroxy groups;

keto, ketal and acetal groups derived from lower aliphatic or aralkyl alcohols;

ketoxime, aldoxime or hydrazone groups optionally substituted by lower alkyl or aralkyl groups;

free mercapto groups or mereapto groups esterified with a lower aliphatic or araliphatic acid or etherified with lower aliphatic or araliphatic alcohols;

free or esterified carboxy groups;

free sulfonic acid groups or sulfonic groups esterified with lower aliphatic or araliphatic alcohols;

sulfamide or sulfamidic groups substituted by lower alkyl or aralkyl groups or lower alkylene groups;

sulfoxide or sulfone groups derived from lower alkyl or aralkyl groups;

nitrile groups;

free or substituted amino groups, and quaternary ammonium derivatives of such amino groups; or esters and/or amides of the sialic carboxy groups of said N-acyl-lysogangliosides, inner esters of said N-acyl-lysogangliosides, metal salts or organic base salts of said N-acyl-lysogangliosides having acid groups, acid addition salts of said N-acyl-lysogangliosides and the corresponding derivatives of mixtures of said N-acyl-lysogangliosides.

The invention is also directed to pharmaceutical preparations containing one or more of the above-mentioned derivatives of lysogangliosides or their mixtures, or the respective salts, as well as their therapeutic use and methods for their preparation.

Figure 1:
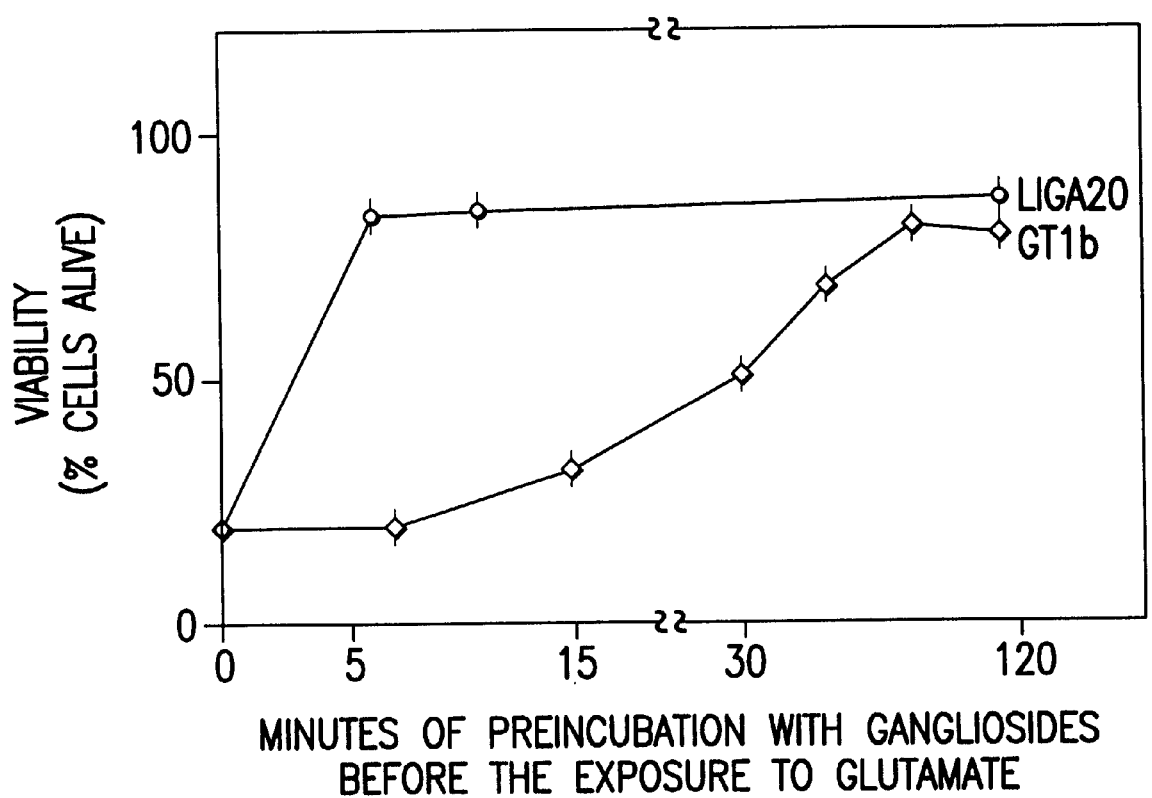
FIG. 1 shows the protective effect of gangliosides against glutamate-induced neurotoxicity. Glutamate is present at 50 $\mu$M, GT1b is present at 60 $\mu$M, and LIGA20 is present at 7 $\mu$M.

The acylation of lysogangliosides is already known and N-acyl derivatives have already been prepared which are similar to those of the present invention; see the publication "Lysogangliosides: Synthesis and Use in Preparing Labeled Gangliosides" by Gunther Schwarzmann and Konrad Sandhoff in "Methods in Enzymology", Vol. 138, pp. 319–341 (1987). They have been used in biochemical studies concerning the action of gangliosides on cell membranes, using suitably labelled acyl groups. The N-acyl lysogangliosides described in this publication are essentially derived either from nonaliphatic acids, or from aliphatic acids substituted by different groups from those of the present invention. However, in one of the described preparation methods of those lysogangliosides (having a well-defined sphingosine chain, unlike the derivatives of the present invention), a sphingosine is used wherein the hydroxy group is protected in the 3-position with a benzoyl group, and the amino nitrogen in the 2-position is protected with an acyl group derived from dichloroacetic acid. This reagent leads, by condensation with a residue derived from the oligosaccharide-sialic part of the ganglioside $GM_1$, to an intermediate product constituted by N-dichloroacetyl lysoganglioside $GM_1$ benzoylated in the noted position of the sphingosine residue. The dichloracetyl lyso $GM_1$ of the present invention described, for example, in illustrative Example 3, was not prepared by that synthesis, both the above-mentioned benzoyl group and the dichloroacetic acid group being simultaneously eliminated at a subsequent stage.

A derivative protected by similar benzoyl and dichloroacetic groups, respectively, is also described in the Schwarzmann, et al. publication with regard to the preparation of lyso $GM_3$ ganglioside, but in this case also lyso $GM_3$ dichloroacetyl was not prepared.

The lysogangliosides which serve as the basis for the preparation of the new N-acyl derivatives according to the present invention are obtainable by deacylation of the gangliosides extractable from natural products, and especially from tissues of the central or peripheral nervous systems of vertebrates, but also from adrenal marrow, from erythrocytes, from the spleen or other organs. They may be purified gangliosides, such as those described in the literature, those which may be traced back to a unitary structure with respect to their saccharide part, or they may be ganglioside mixtures. Among the most important gangliosides for use as the starting material for the new derivatives of the invention are, for example, those in which the oligosaccharide is formed by a maximum of 4 hexose residues, and in which this saccharide part is chemically unitary. The hexoses should preferably be chosen from the group formed by N-acetylglucosamine and N-acetylgalactosamine (ganglioside group A). The gangliosides belonging to this group are, for example, those extracted from vertebrate brains, such as those described in the article: "Gangliosides of the Nervous System" in "Glycolipid Methodology", Lloyd A. Witting Ed., American Oil Chemists Society, Champaign, Ill. 187–214 (1976) (see particularly Table 1). These include the gangliosides $G_{M4}$, $G_{M3}$, $G_{M2}$, $G_{M1}$-GlcNAc, $G_{D2}$, $G_{D1a}$-GalNac, $G_{T1c}$, $G_Q$, $G_{T1}$ and, particularly, those in which the oligosaccharide moiety contains at least one glucose or galactose residue and one of N-acetylglucosamine or N-acetylgalactosamine and above all the following (ganglioside group B):

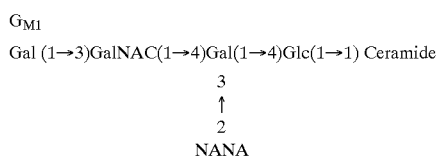

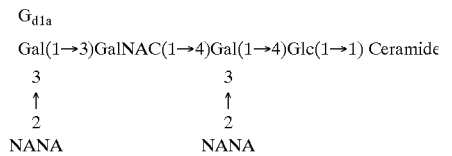

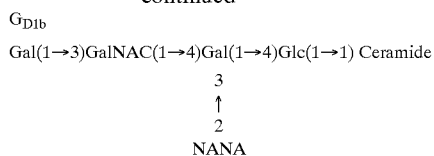

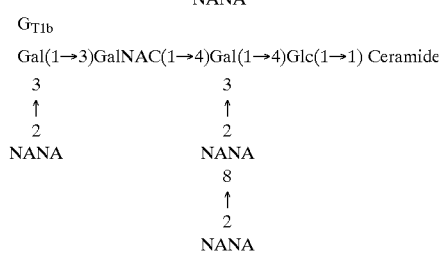

wherein Glc stands for glucose, GalNAC stands for N-acetylgalactosamine, Gal stands for galactose, and NANA stands for N-acetylneuraminic acid.

To better illustrate the structure of the gangliosides of the above formula, which is substantially the same as that of the derivatives of the present invention, and in saccharide part, the sialic acids and the ceramide, the following is the entire formula of a "pure" ganglioside $GM_1$ containing a single sialic acid (represented by N-acetylneuraminic or N-glycolylneuraminic acid):

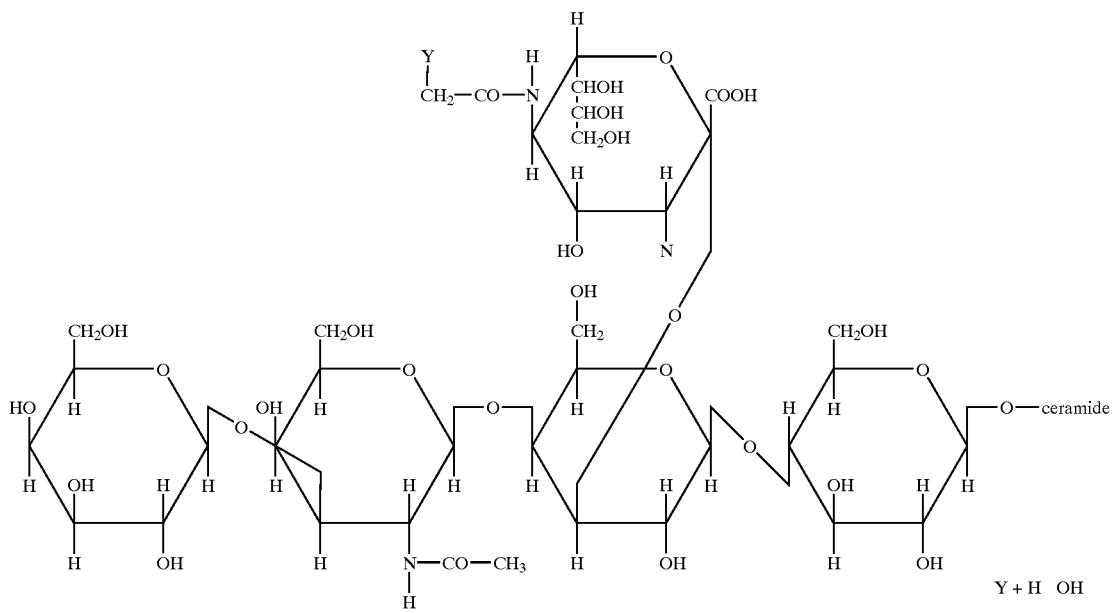

The same formula is essentially also valid for a derivative of the ganglioside $GM_1$ according to the present invention, taking the ceramide residue to be substituted by a corresponding "artificial" ceramide, in which the N-acyl group is derived from one of the said aliphatic acids substituted by polar groups. Also included in the present invention are mixtures of the new N-acyl lysogangliosides and in particular those derived from ganglioside mixtures such as those present in extracts from various animal tissues, such as in "total" extracts, or in various fractions, for example those described in the literature. Such extracts and fractions are described in the articles cited above and also in the following articles: "Extraction and Analysis of Materials Containing Lipid Bound Sialic Acid", in said publication, pages 159–186 (1976) and in "Gangliosides of the Nervous System" in the same book, pages 187–214, and in German patent No. 25 49 680. In such mixtures the N-acyl part of the ganglioside mixtures is substituted by one of the said acyl groups. These derivatives may be obtained according to the procedure of the present invention as reported herein for the deacylation of the ganglioside mixtures and subsequent reacylation, optionally after the reacylation of other deacylated groups in the sialic part of the gangliosides. Among the most important ganglioside mixtures to be used as starting products are ganglioside extracts obtained from the nervous system, in particular from the brain and containing the gangliosides $GM_1$, $G_{D1a}$, $G_{D1b}$ and $G_{T1b}$.

It is already known that gangliosides play an important role in the nervous system and it has recently been demonstrated that gangliosides are useful in therapy for pathologies affecting the peripheral nervous system and in pathologies affecting the central nervous system [Acta Psychiat. Scand., 55, 102, (1977); Eur. Medicophys., 13, 1, (1977); Ric. Sci. Educ. Perm. Suppl. 9, 115, (1978); Adv. Exp. Med. Biol. 71, 275, (1976); Electromyogr. Clin. Neurophysiol., 19, 353, (1979); Minerva Medica, 69, 3277, (1978); Minerva Stomat., 27, 177, (1978); Med. del Lavoro, 68, 296 (1977); Brain Res. 197, 236, (1980)].

The therapeutic action of gangliosides seems to involve stimulating sprouting phenomena of the nerve cells and in activating the membrane enzymes involved in the conduction of nervous stimuli such as the enzyme (Na+,K+)ATPase [Brain Res., 197, 236 (1980), J. of Neurochem. 37, 350 (1981)]. Ganglioside-stimulated neuronal sprouting enhances functional recovery of the affected nerve tissue.

Further studies have been carried out to find compounds which may be more efficacious than gangliosides in therapy for pathologies of the nervous system. Such studies have led, for example, to the discovery that ganglioside inner esters, in which one or more of the hydroxyl groups of the saccharide part are esterified with one or more carboxy groups of the sialic acids (an intramolecular reaction) with the formation of the same number of lactone rings, are more active than gangliosides themselves in enhancing neuronal sprouting and in activating the membrane enzymes involved in nerve stimulus conduction. An example is the enzyme (Na+,K+)ATPase (see U.S. Pat. Nos. 4,476,119, 4,593,091 and 4,716,223).

Improved neuronal sprouting activity and nerve stimulus conduction are also observed with the "outer" esters of gangliosides, that is, esters of the carboxy functions of sialic acids with various alcohols of the aliphatic, araliphatic, alicyclic or heterocyclic series. Ganglioside amides also possess the same properties, as well as peracylated derivatives of both amides and esters and of simple gangliosides. All of these derivatives, which are described in U.S. Pat. No. 4,713,374, are also to be considered basic substances for the new N-acyl derivatives of the present invention.

The new ganglioside derivatives of the invention possess interesting pharmacological properties, and more precisely an inhibiting action on the activation of protein-kinase C which may prove to be undesirable and negative in certain conditions involving the imbalance of normal neurotransmission functions. Activation is triggered by an increased concentration of excitatory amino acids such as glutamic acid and/or aspartic acid; these acids have, in such abnormal conditions, a direct toxic action on neuronal cells. One great advantage of the products of the present invention, which sets them apart from other protein-kinase C inhibitors such as gangliosides themselves or sphingosine, consists in their ability to prevent and combat the abovesaid neurotoxic action. It should be emphasized that the products of the present invention, unlike calcium antagonists and glutamate receptor antagonists (NMDA in particular), only act in the presence of abnormal conditions, and they therefore limit neurotoxicity and maintain neuronal plasticity, thereby allowing a more facile recovery of damaged physiological functions. The abovesaid pharmacological properties of the new N-acyl lysogangliosides can be illustrated by the following experiments conducted on N-dichloroacetyl lyso $GM_1$ and on N-monochloroacetyl lyso $GM_1$.

Effect of N-acyl Lysogangliosides on Protection of the Neurotoxic Effects of Excitatory Amino Acids In primary cultures of cortical and cerebral rat neurons, the excitatory amino acids (EAA) regulate protein kinase C (PKC) activation and translocation and induce cell death. In particular, the addition of glutamate to these cell cultures induces damage probably caused by the influence of Ca+2, induced by glutamate itself, followed by translocation and then activation of PKC. Vaccarino et al [Proc. Natl. Acad. Sci. USA 84, 8707–8711 (1987)], Hannun Y. A. et al. [J. Biol. Chem. 261, 12604–12609 (1986)], Merrill A. H. et al. [J. Biol. Chem. 261, 12610–12615 (1986)], Wilson E. et al. [J. Biol. Chem. 261, 12616–12623 (1986)], and Hannun Y. A. et al. [Science 235, 670–673 (1987)] have reported that exposure of cerebral granule cells to gangliosides (trisialosyl-N-tetraglycosylceramide-$G_{T1b}$ or monosialosyl-N-tetraglycosyl-ceramide-$GM_1$) inhibits translocation and activation of PKC induced by glutamate. These gangliosides prevent the interaction of glutamate with its high affinity recognition site and with [$^3$H] PDBu binding. Furthermore, such gangliosides offer protection from glutamate-induced cell damage. Studies conducted using the new ganglioside derivatives N-dichloro acetyl lyso-$GM_1$ and N-monochloro acetyl lyso $GM_1$ compared to ganglioside fractions ($GM_1$ and $GT_{1b}$) are described below. In particular, the effects of the derivatives of this invention on glutamate-induced neurotoxicity in vitro and in vivo and on PKC translocation in primary cultures of cerebral granule cells were studied.

Materials and Methods

In Vitro Studies 1.a. Primary cultures of cerebral granule cells from 8-day-old Sprague Dawley rats (Zivic Miller) [Gallo V. et al., Proc. Natl. Acad. Sci. USA 79, 7919–7923 (1982)]. These cultures contain >90% of granule cells, <5% of GABAergic neurons and <5% of glial cells [Vaccarino F. M. et al., J. Neurosci. 7, 65–76 (1987)]. The cells were used for the experiments on the 8th and 9th days of culture.

1.b. Substances added to the culture (method and parameters).

On the 8th and 9th days of culture, concentrations varying between 7 and 100 μM of the following substances are added: N-dichloro acetyl lyso $GM_1$, N-monochloro acetyl lyso $GM_1$, $GT_{1b}$, $GM_1$. More particularly, the monolayers of granule cells are preincubated with these compounds in Locke's solution (1 ml) for 120 minutes (or for periods of time varying between 0 and 120 minutes) at 37° C. Gangliosides and derivatives are previously dissolved and subsequently diluted, if necessary, in methanol: $H_2O/95:5$. Aliquots of the solution are dried in a $N_2$ current and gathered with a suitable volume of Locke's solution until the final concentration is reached.

1.c. Glutamate-induced neurotoxicity.

The neurotoxic effect of glutamate was assessed under various experimental conditions:

Influence of incubation time (0–120° C.) of the substances before exposure to glutamate: intact cells are preincubated with N-dichloro acetyl lyso $GM_1$, N-monochloro acetyl lyso $GM_1$ (7 μM) and $GT_{1b}$ (60 μM) at 37° C. After removal of excess compound by washing, the cells are incubated with 50 μM of glutamate in the absence of Mg+2 for 15 minutes at room temperature after which the cells are washed three more times and then replaced in the medium. Cell survival is assessed after 24 hours by histochemical techniques, or after iodide-fluorescein diacetate staining which gives green fluorescence to live cells and red to non-living cells.

Influence of the time interval between pre-treatment with ganglioside derivatives or gangliosides themselves and exposure to glutamate: intact granule cells are preincubated for 2 hours at 37° C. with N-dichloro acetyl lyso $GM_1$ (7 μM) $GT_{1b}$ and $GM_1$ (100 μM). Excess compound is removed by washing and the cells exposed to 50 $\mu$M of glutamate (in the absence of $Mg^{+2}$) for 15 minutes after various time intervals (1, 2, 4, 6, 12, 18, 24 and 48 hours).

Effect of simultaneous treatment with glutamate and gangliosides: intact granule cells are treated (15 and 35 minutes) with 50 $\mu$M of glutamate and the gangliosides N-dichloro acetyl lyso $GM_1$ (7 $\mu$M), $GT_{1b}$ and $GM_1$ (100 $\mu$M). In the first type of experiment (cotreatment for 15 minutes) the excess compound is removed by washing, and then cell survival is assessed according to the described method. In the second type of experiment (cotreatment for 30 minutes) the cotreatment is prolonged for another 35 minutes of exposure to gangliosides.

Effect of N-dichloro acetyl lyso $GM_1$ following intermittent exposure to glutamate: granule cells are exposed intermittently to glutamate and treated with N-dichloro acetyl lyso $GM_1$ (7 $\mu$M) for 20 minutes (in the absence of Mg2+). The excess product is removed by washing.

Effect of N-dichloro acetyl lyso $GM_1$ following cell anoxia (in $N_2$ chamber) on protection from endogenous glutamate-induced neurotoxicity. Cell viability is assessed by colorimetry after 24 hours (MTT stains only live cells).

1.d. Translocation of PKC induced by glutamate: assessment of [3H]-phorbol ester binding on intact cells.

The effects of binding of [3H]-phorbol ester are assessed under two different types of experimental conditions:

cotreatment for 15 minutes with 50 $\mu$M of glutamate, gangliosides and the derivatives N-dichloro acetyl lyso $GM_1$ (7 $\mu$M), $GT_{1b}$ and $GM_1$ (100 $\mu$M)

cotreatment for 30 minutes with 50 $\mu$M glutamate and N-dichloro acetyl lyso $GM_1$ (7 $\mu$M), $GT_{1b}$ and $GM_1$ (100 $\mu$M), followed by further exposure (35 minutes) to gangliosides. After cotreatment the cells-are washed and [$^3$H]-PDBu binding is assessed in the presence of $Mg^{+2}$. Granule cells are grown on discs measuring 35 mm in diameter and then washed and incubated with Locke's solution containing 4-B-[$^3$H]-phorbol-12, 13-dibutyrate [$^3$H]-P(Bto)$_2$, 12.5 Ci/mmol (1 Ci=37 GBq; New England Nuclear), in 0.1% fatty acid-free bovine albumin serum (Sigma Chemical Co.). Since preliminary experiments showed that a balance is reached within 10 minutes, the cells are incubated with [$^3$H]-P(Bto)$_2$ for 15 minutes at 22° C. The binding is constant for over one hour. After incubation the cells are washed 3 times with cold Locke's solution and suspended with NaOH 0.1M. The aliquots of suspension are used for protein determination [Lowry O. H. et al., J. Biol. Chem. 193, 256–275 (1951)]. Non-specific binding is assessed in the presence of 2 $\mu$M phorbol 12-tetradecanoate 13-acetate (PTA).

2.a. Cell cultures.

Mouse neuroblastoma cells ($N_2$A) at the 180th passage are placed in wells at a concentration of 10,000 cells per well (COSTAR-24). The next day the medium was substituted with 350 $\mu$l of DMEM+P/G+10% FCS.

2.b. Compounds added to the culture: addition method and parameters observed.

All compounds are dissolved in chloroform/methanol 2:1 dried in $N_2$ current and resuspended in DMEM+P/G+10% FCS. The number of neurites is assessed 24 hours later.

In Vivo Studies

Newborn rats (7 days old) weighing about 13 g are injected with 25 nmol NMDA i.c.v. Under these conditions the excitotoxin induces a decrease of 28% in weight of the injected hemisphere and a mortality rate of 53.6%.

Administration of the compounds: injection method and parameters observed. The rats were treated with N-dichloro acetyl lyso $GM_1$ and N-monochloro acetyl lyso $GM_1$ at a dose of 200 $\mu$mol/animal s.c., 1 hour before and immediately after injection of NMDA. The compounds were solubilized in PBS. The N-dichloro acetyl lyso $GM_1$ and N-monochloro acetyl lyso $GM_1$ derivatives were tested in comparison to magnesium sulfate, MK-801 (a non-competitive agonist of the NMDA receptor) [G. McDonald et al., Eur. J. Pharmacol. 140: 153–157 (1987)] and kinurenic acid [P. Andiné, Neuroscience Letters, 90: 208–212 (1988)] which is capable of diminishing brain damage. Mortality was assessed 5 days after MNDA injection.

Results

The experiments showed that in vitro, in cerebral granule cells:

pretreatment for 2 hours with N-dichloro acetyl lyso $GM_1$ (LIGA 20) and $GT_{1b}$ almost totally prevents glutamate-induced neurotoxicity (FIG. 1). It should be noted that the protection offered by N-dichloro acetyl lyso $GM_1$ (7 $\mu$M) is already evident after only 5 minutes of preincubation, while in the case of $GT_{1b}$ (60 $\mu$M) it is significant, although to a lesser degree, following incubation for 60 minutes. It is also interesting to note that the maximum effect exercised by N-dichloro acetyl lyso $GM_1$ requires a concentration more than 8 times less than that of $GT_{1b}$ (7 $\mu$M vs 60 $\mu$M).

Figure 2:
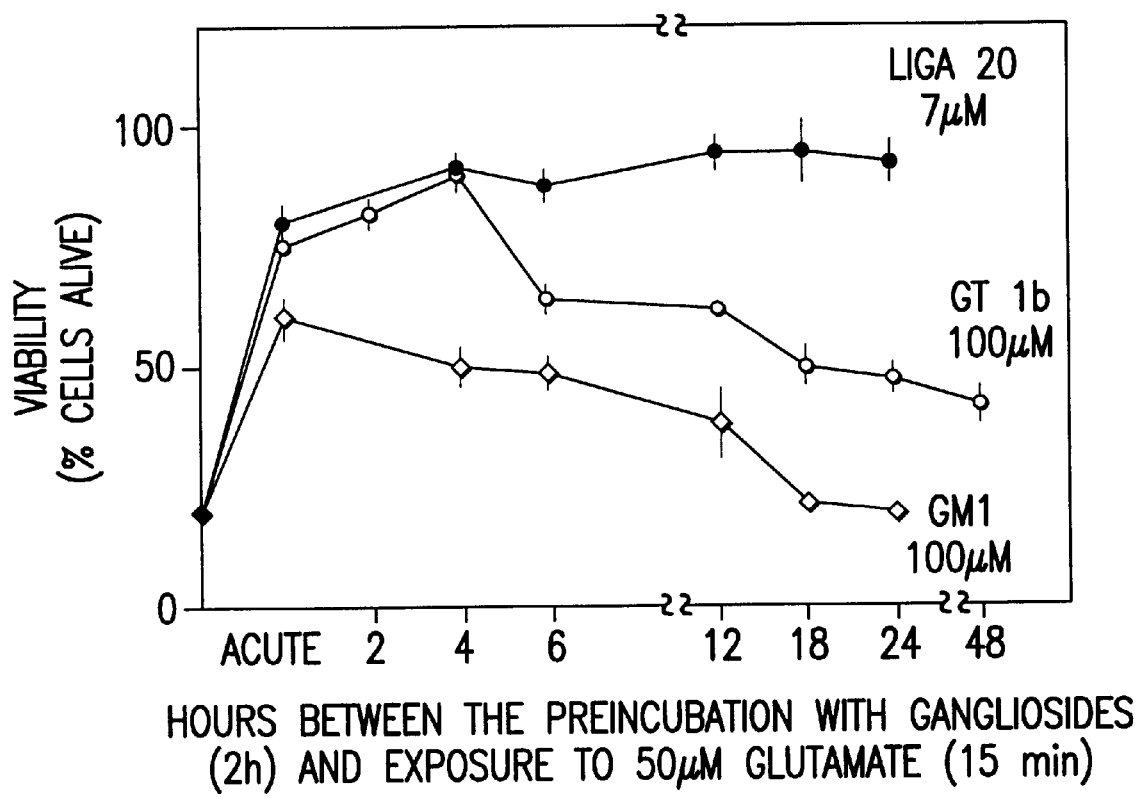
FIG. 2 shows the influence of the time interval between pretreatment with gangliosides and exposure to glutamate on cell survival.

The protective effect of N-dichloro acetyl lyso $GM_1$ on glutamate-induced neurotoxicity persists for at least 24 hours after removal of the medium, while that of $GT_{1b}$ persists for 4 hours (FIG. 2) and that of $GM_1$ persists for no more than 1 hour ($GM_1$<$GT_{1b}$<N-dichloro acetyl lyso $GM_1$).

Figure 3:
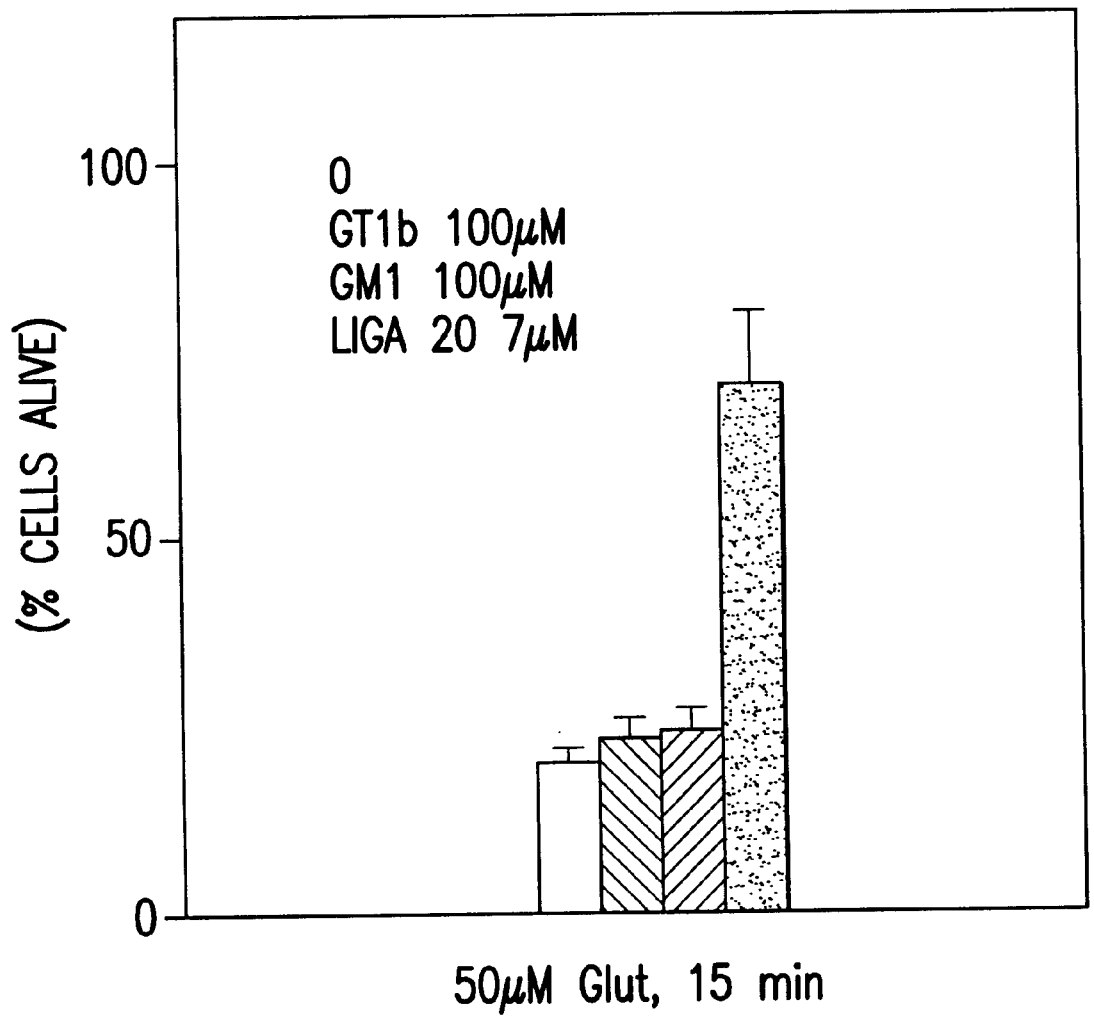
FIG. 3 shows the effect of cotreatment (15 min.) with glutamate and gangliosides on cell survival.
Figure 4:
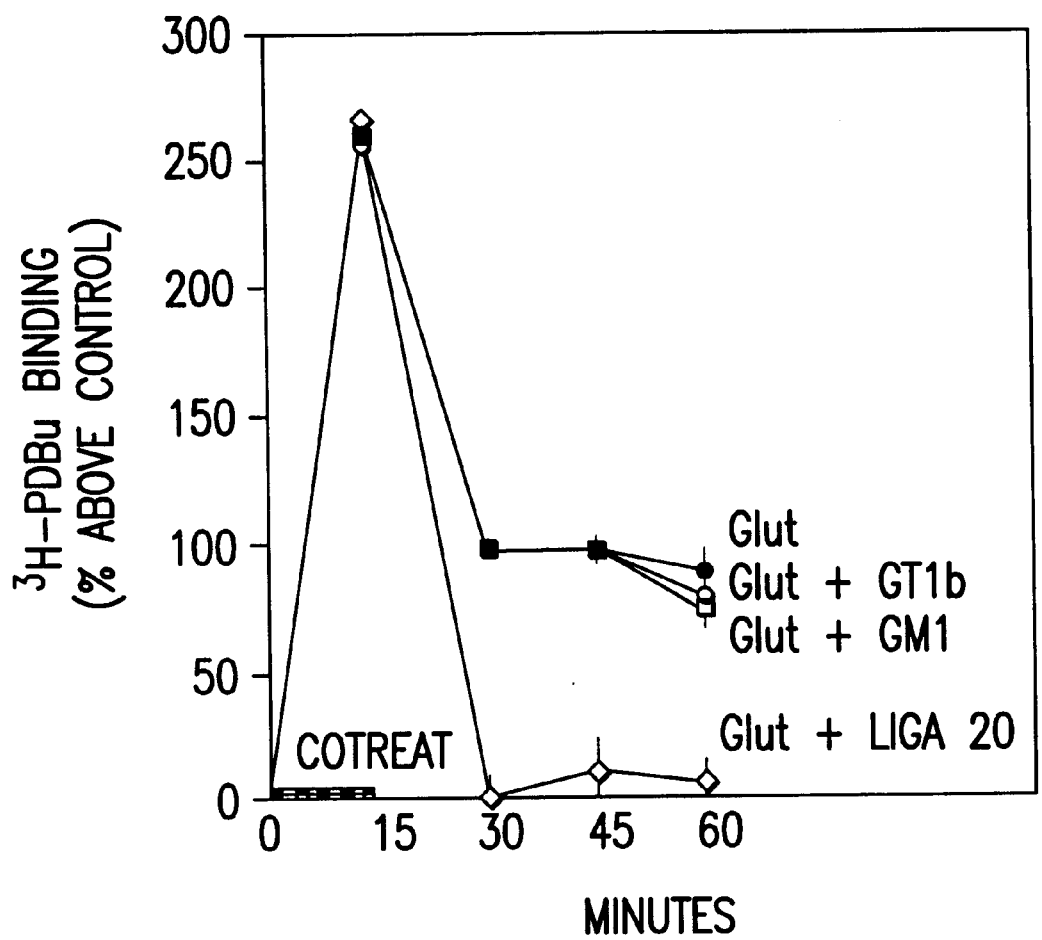
FIG. 4 shows the effect of cotreatment (15 min.) with glutamate (50 $\mu$M) and gangliosides (100 $\mu$M) GM1, GT1b or 7 $\mu$M LIGA 20 on $^3$H-PDBu binding.
Figure 5:
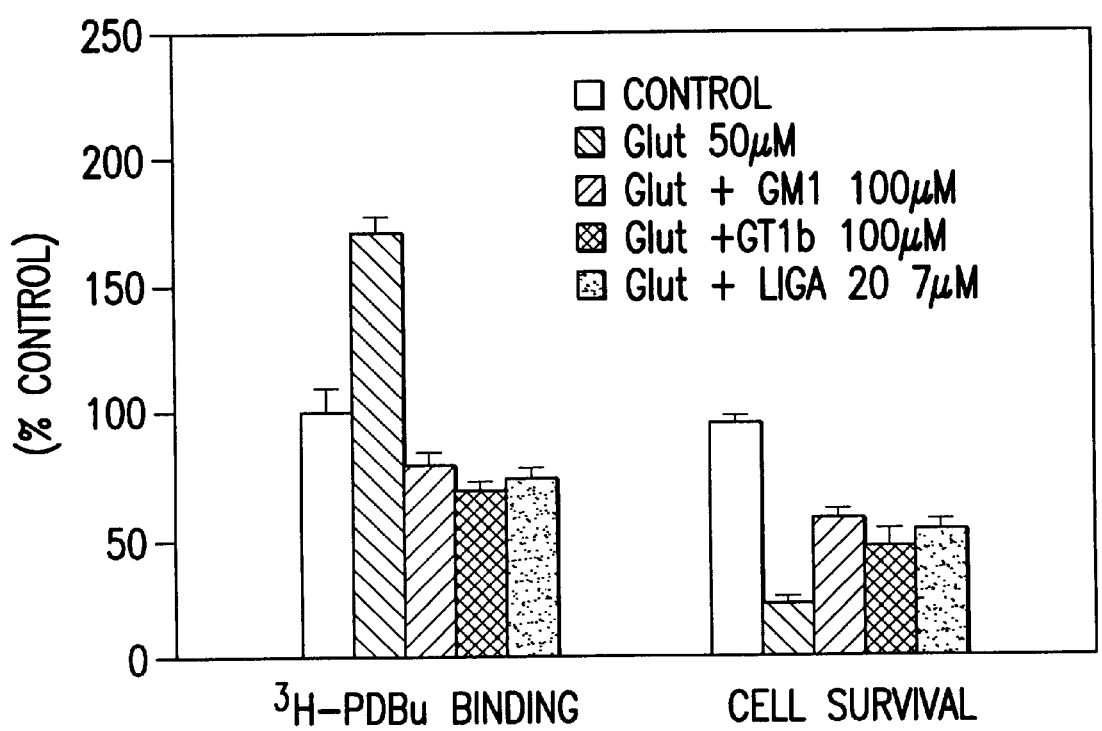
FIG. 5 shows the effect of cotreatment (35 min.) with glutamate and gangliosides followed by prolonged exposure (an additional 35 minutes) to gangliosides on $^3$H-PDBu binding and on cell survival.

Cotreatment (15 minutes) with glutamate and N-dichloro acetyl lyso $GM_1$ is effective in protecting cells from the neurotoxic effect of glutamate while treatment with $GT_{1b}$ and $GM_1$ is not (FIG. 3). In parallel, cotreatment with N-dichloro acetyl lyso $GM_1$ and glutamate inhibits PKC translocation induced by glutamate with maximum activity after 30 minutes (FIG. 4). Also effective is cotreatment for 35 minutes (FIG. 5) and subsequent prolonged incubation time with gangliosides both in protecting from neurotoxic effect and in inhibiting PKC translocation. In these experimental conditions the values obtained with N-dichloro acetyl lyso $GM_1$ are comparable to those obtained with $GM_1$ and $GT_{1b}$. It is important to note that the effect of N-dichloro acetyl lyso $GM_1$ can still be considered superior to that of $GM_1$ and $GT_{1b}$ since it is obtained with much lower doses (7 $\mu$M vs 100 $\mu$M).

Figure 6:
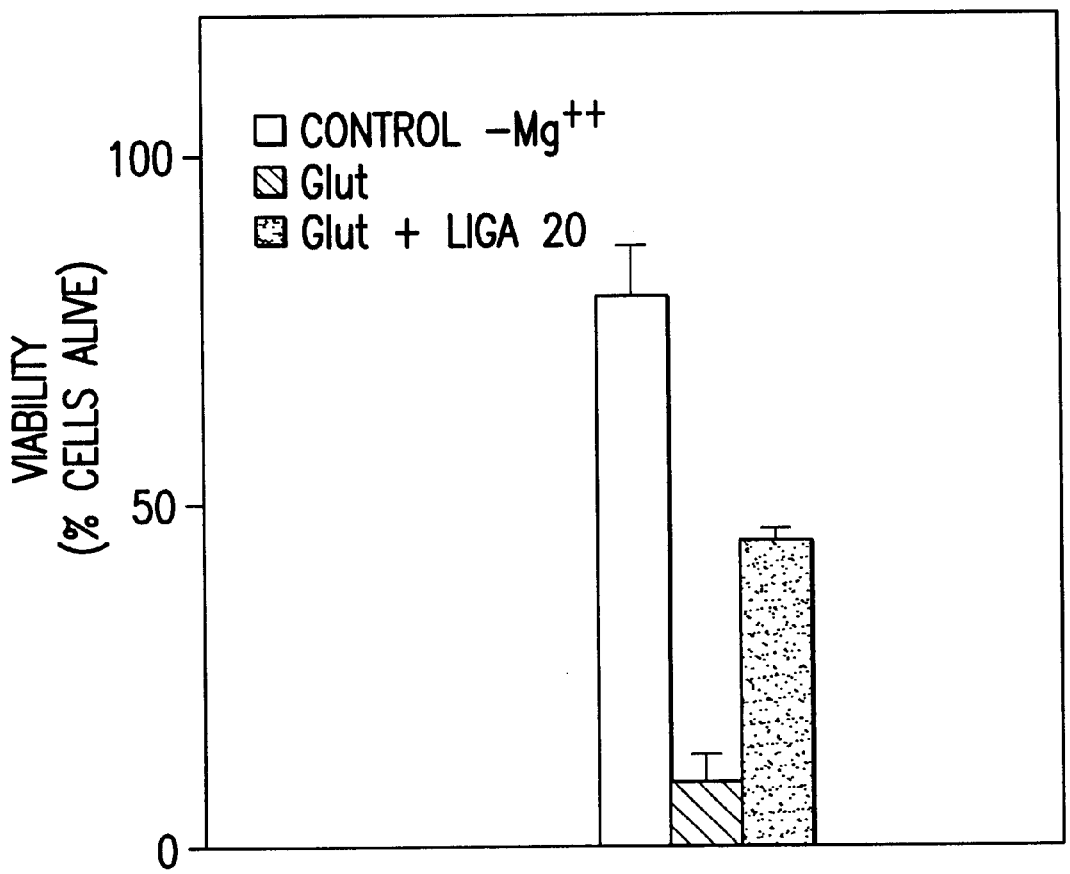
FIG. 6 shows the treatment with LIGA 20 (7 $\mu$M) for 20 minutes after glutamate administration which prevents glutamate-induced neurotoxicity.

Post-treatment (20 minutes) with N-dichloro acetyl lyso $GM_1$ is also active in reversing the neuronotoxic effect induced by glutamate administered intermittently (FIG. 6).

Figure 7:
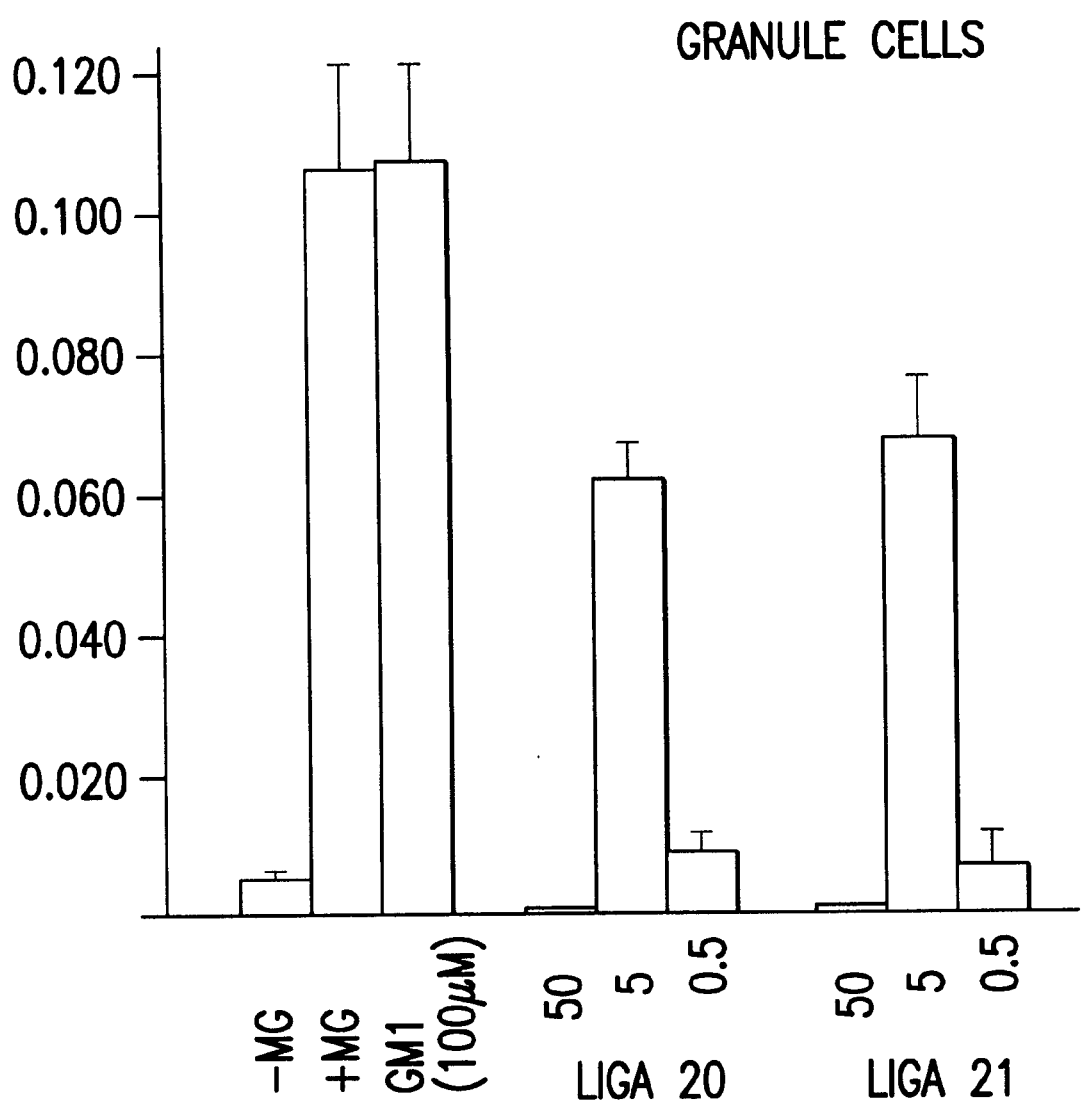
FIG. 7 shows anoxia induced by $N_2$. Pretreatment was performed with LIGA 20 and 21 for 10 minutes, and with $GM_1$ for 60 minutes. The cells are washed with serum and placed in anoxic conditions in the absence of $Mg^{+2}$ for 5 hours and replaced in the culture medium. Cell viability was measured 24 hours after with MTT.

N-dichloro acetyl lyso $GM_1$ and N-monochloro acetyl lyso $GM_1$ (LIGA 21) are active in protecting against endogenous glutamate-induced neurotoxicity under anoxic conditions (FIG. 7).

N-monochloro acetyl lyso $GM_1$ shows a pharmacological outline comparable to that of N-dichloro acetyl lyso $GM_1$ (protection in the range of 10 $\mu$M).

In the in vivo studies, N-dichloro acetyl lyso $GM_1$ and N-monochloro acetyl lyso $GM_1$ protected the test animals from mortality following i.c.v. injection of NMDA which produces damage comparable to that induced by ischemia. The effect of N-dichloro acetyl lyso $GM_1$ and N-monochloro acetyl lyso $GM_1$ is comparable to that demonstrated by $Mg^{+2}$ or by kinurenic acid (Table 3).

TABLE 1

Neuritogenic activity in N2A cells

| | | Morphology (24 hr) % of cells with neurites | $^3$H Tdr. (48 hr) n = 3 | MTT (48 hr) n = 3 |
|---|---|---|---|---|
| Control | | <5 | 40271 ± 3584 (n = 6) | 0.284 ± 0.01 (n = 6) |
| Control + DMSO | | <5 | nd | nd |
| GM1 1 × $10^{-4}$ M | | 70–80 | 40834 ± 1885 | 0.259 ± 0.007 |
| LIGA 21 | 1 × $10^{-4}$ M | 80–90 | 14256 ± 1594 | 0.158 ± 0.01 |
| | 5 × $10^{-5}$ M | 80–90 | 36016 ± 5030 | 0.243 ± 0.008 |
| | 5 × $10^{-6}$ M | <5 | 43035 ± 487 | 0.324 ± 0.01 |
| LIGA 22 | 1 × $10^{-4}$ M | <5 | nd | nd |

LIGA 21 = N-monochloro acetyl lyso $GM_1$
LIGA 22 = N'-monochloro acetyl lyso $GM_1$

TABLE 2

N2 anoxia
(Granule cells)
(1) Cultures are pretreated as indicated, then washed, placed in anoxic conditions (in $N_2$ chamber) and then returned to original medium: they are reacted with MTT after 24 hours. Anoxia is usually effected in the absence of $Mg^{2+}$.

| Pretreated | MTT O.D. (570–630) |
|---|---|
| Control (+ $MG^{2+}$) | 0.145 ± 0.007 (100%) |
| $GM_1$ (100 μM, 60 min) | 0.160 ± 0.010 (110%) |
| N-dichloro acetyl lyso $GM_1$ (5 μm, 10 min) | 0.163 ± 0.012 (112%) |
| N-monochloro acetyl lyso $GM_1$ (5 μm, 10 min) | 0.152 ± 0.013 (105%) |

TABLE 3

NMDA-induced neurotoxicity in new-born rat

| | dose | | mortality | relative |
|---|---|---|---|---|
| TREATMENT | nMoli/ animal | mg/kg | (deceased/ treated) | mortality (% of treated) |
| Saline icv + PBS sc | — | | 1/32 | 3.1 |
| NMDA icv + PBS sc | — | | 22/41 | 53.6 |
| NMDA + $AGF_2$ sc | 200 | 25 | 3/17 | 17.6 |
| NMDA + $AGF_2$ sc | 100 | 25 | 0/9 | 0 |
| NMDA + $AGF_2$ sc | 15 | 1.85 | 0/8 | 0 |
| NMDA icv + LIGA 20 sc | 200 | 28 | 1/8 | 12.5 |
| NMDA icv + LIGA 21 sc | 200 | 21 | 0/8 | 0 |
| NMDA icv + MK 801 i.p. | 75 | 2 | 6/16 | 37 |

The animals (aged 7 days, weighing 13 grams) were treated at the doses and by the route indicated in the Table, 1 hr before and again immediately after injection of NMDA (25 nMoli i.c.v.). Mortality was assessed up to 5 days after treatment
LIGA 20 = N-dichloro acetyl lyso $GM_1$
LIGA 21 = N-monochloro acetyl lyso $GM_1$ Toxic Potential
1. Hemolysis in Rabbit Blood Method: 100 μl of compound in solution is incubated in 1 ml of fresh rabbit blood (500 USP units of sodium heparin/12 ml blood) for 5 minutes at room temperature. After centrifugation (3000 rpm., 3 min) the diluted plasma is measured by spectrophotometry (wavelength=545 nm). Hemolytic activity is expressed as a percentage of sphingosine-induced hemolysis.

Results: The N-acyl lyso derivatives do not induce hemolysis in rabbit blood up to a concentration of 1 mM.
2. Neurotoxicity Neurotoxicity of N-acyl lyso derivatives of $GM_1$ was tested in primary cultures of cerebral granule cells. FDA-PI staining is conducted after 24 hours and after a two-hour incubation with the compounds.

Results: The N-acyl lyso derivatives tested induce neurotoxicity at concentrations of at least twice the active concentrations. Because of the pharmacological properties described above, the N-acyl lysoganglioside derivatives of the present invention can be used as drugs in the following pathologies: cerebral ischemia, metabolic encephalopathies such as hypoglycemia and hypoxia, encephalopathies of toxic origin, trauma, aging, epilepsy, neurodegenerative diseases such as Parkinson's disease and Huntington's chorea and mental disorders.

All of the derivatives of the N-acyl lysogangliosides of the invention, such as esters, inner esters, amides and peracylates, can be obtained by the same procedures as described in the prior art for derivatives corresponding to gangliosides. The invention also includes in particular mixtures of these derivatives, such as are obtained from mixtures of N-acyl lysogangliosides according to the invention, obtained in turn from the said mixtures of gangliosides.

The ester groups in the novel N-acyl lysoganglioside derivatives are derived in particular from alcohols of the aliphatic series and especially from those having a maximum of 12, especially up to 6 carbon atoms, or of the araliphatic series with preferably only one benzene ring optionally substituted by 1 to 3 lower alkyl groups ($C_{1-4}$), for example methyl groups, and a maximum of 4 carbon atoms in the aliphatic chain, or by alcohols of the alicyclic or aliphatic-alicyclic series with only one cycloaliphatic ring and a maximum of 14 carbon atoms or of the heterocyclic series with a maximum of 12, especially up to 6 carbon atoms and only one heterocyclic ring containing a heteroatom chosen from the group formed by N, O and S.

The amide groups of the carboxy functions in the N-acyl lysoganglioside derivatives of the present invention are derived from ammonia or from amines of any class having preferably a maximum of 12 carbon atoms.

The alcohols and amines may be unsubstituted or substituted, especially by functions chosen from the group formed by hydroxy, amino, alkoxy groups with a maximum of 4 carbon atoms in the alkyl moiety, carboxy or carbalkoxy groups with a maximum of 4 atoms in the alkyl moiety, alkylamino or dialkylamino residues with a maximum of 4 carbon atoms in the alkyl moiety, which may be saturated or un-saturated, especially with only one double bond.

The alcohols which esterify the carboxy functions of the N-acyl lysogangliosides according to the present invention may be monovalent or polyvalent, in particular bivalent.

Of the alcohols of the aliphatic series, special mention should be made of the lower alcohols having a maximum of 6 carbon atoms, such as methyl alcohol, ethyl alcohol, propyl and isopropyl alcohol, normal-butyl alcohol, isobutyl alcohol, tertiary-butyl alcohol, and of the bivalent alcohols such as ethylene glycol and propylene glycol. Of the alcohols of the araliphatic series, special mention should be made of those with only one benzene residue, such as benzyl alcohol and phenethyl alcohol. Of the alcohols of the alicyclic series, preference should be given to those with only one cycloaliphatic ring, such as cyclohexyl alcohol (cyclohexanol), or terpene alcohols, such as menthanol, carvomenthol, or one of the terpineols or terpinenols or piperitol. Of the alcohols of the heterocyclic series, special mention should be made of tetrahydrofuranol or tetrahydropyranol. To esterify the carboxy groups of the N-acyl lysogangliosides, it is possible to use also aliphatic alcohols, substituted, for example, by amino functions, such as amino alcohols having a maximum of 4 carbon atoms and especially amino alcohols with a dialkyl ($C_{1-4}$)-amino group such as diethylaminoethanol.

The carboxamide functions according to the present invention are either derived from ammonia (and the amide in this case is the unsubstituted amide —$CONH_2$) or from primary or secondary amines, especially from those containing a maximum of 12 carbon atoms. Such amines may be of an aromatic, heterocyclic, alicyclic, but especially aliphatic nature. Preferred embodiments of the present invention are the carboxamide derivatives of aliphatic amines with a maximum of 12 carbon atoms, and these amines may have open, straight or branched chains or may be cyclic, such as the alkylamines derived from alkyl groups having between 1 and 6 carbon atoms, such as methylamine, ethylamine, propylamine, hexylamine, dimethylamine, diethylamine, diisopropylamine, dihexylamine, or the alkylene amines derived from alkylene groups with straight chains having between 3 and 6 carbon atoms or corresponding chains substituted by 1 to 3 methyl groups, such as pyrrolidine, piperidine and azepine. The alkyl or alkylene groups of these amines may also be interrupted in the carbon atom chain or substituted by other heteroatoms, in particular by nitrogen atoms. The amides of the invention are derived in this case from diamines, for example, ethylenediamine, trimethylenediamine or piperazine. If alkyl or alkylene groups are interrupted or substituted by atoms of oxygen or sulphur, the amides represent derivatives of amino alcohols, such as aminoethanol or aminopropanol or are derivatives of morpholine or thiomorpholine. Of special interest to the present invention are the esters and amides of N-acyl lysogangliosides derived from the gangliosides of groups A and B mentioned above, and of their mixtures.

The invention also includes peracylated derivatives of the hydroxyl groups of the saccharide part, sialic acids and ceramides of the esters and amides described herein. In such derivatives the acyl groups may be derived from acids of the aliphatic, aromatic, araliphatic, alicyclic or heterocyclic series. These acids are preferably acids of the aliphatic series with a maximum of 10 carbon atoms, especially up to 6 carbon atoms, for example, formic, acetic, propionic, butyric, valeric, caproic or caprinic acids. They may also be derived from acids, for instance with the same number of carbon atoms, but substituted, particularly by hydroxyacids, such as lactic acid, by amino acids such as glycine or by dibasic acids such as succinic, malonic or maleic acid. Among the aromatic acids, of particular interest are those with only one benzene nucleus, particularly benzoic acid and its derivatives with methyl, hydroxy, amino or carboxy groups, such as p-aminobenzoic acid, salicylic acid or phthalic acid.

The invention also includes peracylated derivatives of N-acyl lysogangliosides and of the mixtures discussed above, having free carboxy functions. For these derivatives too, particularly important are those acylated derivatives of the acids recited herein. One important group of new derivatives is that comprising gangliosides esterified or converted into amides or peracylated at the hydroxy groups.

The ester groups of such derivatives are formed from aliphatic saturated alcohols having a maximum of 6 carbon atoms, unsubstituted or substituted by hydroxy, alkoxy groups with a maximum of 4 carbon atoms, amino, alkylamino or dialkylamino groups with a maximum of 4 carbon atoms in the alkyl portion, carboxy groups, carbalkoxy groups with a maximum of 4 carbon atoms in the alkyl portion, and by the corresponding alcohols with at the most one double bond, by araliphatic alcohols with only one benzene ring, unsubstituted or substituted by 1 to 3 methyl groups, by cycloaliphatic or aliphatic—cycloaliphatic alcohols with a cyclohexane ring unsubstituted or substituted by 1 to 3 methyl groups and a maximum of 4 carbon atoms in the aliphatic part, by tetrahydrofuranol or by tetrahydropyranol.

The amide groups of such derivatives are derived from ammonia or from alkylamines, dialkylamines or alkyleneamines with a maximum of 6 carbon atoms in the alkyl groups thereof and between 4 and 8 carbon atoms in the alkylene groups and in which the alkyl or alkylene groups may be interrupted in the carbon atom chain by heteroatoms chosen from the group formed by nitrogen, oxygen and sulphur, the amino —NH group, in the case of the presence of a nitrogen atom, being substituted by an alkyl with a maximum of 4 carbon atoms and/or may be substituted by groups chosen from the group formed by amino, alkylamino or dialkylamino groups with a maximum of 4 carbon atoms in the alkyl group thereof, or by hydroxy or alkoxy groups with a maximum of 4 carbon atoms in the alkyl part, or by araliphatic amines with only one benzene ring, optionally substituted by a maximum of 3 methyl groups and having a maximum of 4 carbon atoms in the aliphatic part.

Further derivatives include those in which the acyl groups which esterify the hydroxy groups are derived from saturated or unsaturated aliphatic acids with a maximum of 6 carbon atoms, which may be substituted by a function chosen from the group formed by hydroxy, amino and carboxy groups.

The invention also encompasses pharmaceutically acceptble salts of the N-acyl lyso gangliosides and derivatives thereof.

The N-acyl radical described above, which is characteristic of the compounds according to the present invention, is derived from an aliphatic acid with between 2 and 24 carbon atoms. These acids may be polybasic, but are preferably those having only one carboxy function. They are preferably straight-chained. In the radicals with branched chains, the lateral chains are preferably lower alkyl groups with a maximum of 4 carbon atoms, especially methyl groups. The acyls, especially those with branched chains, have preferably a maximum of 12 carbon atoms, preferably a maximum of 6 carbon atoms. The acyl radicals are preferably saturated, but may also have double bonds, preferably between one and two. The polar groups substituted on the N-acyl radical are preferably between 1 and 3 in number and may be the same or different from each other. Preference is given to compounds with acyl radicals substituted in the $\alpha$-position, especially those with a higher content of carbon atoms and/or the unsaturated compounds.

The polar groups are free functions, such as hydroxy or amino groups, or functional derivatives, such as esters, ethers, ketals, etc. The esters, for example, of the hydroxy groups, may be formed from acids of the aliphatic, aromatic, araliphatic, alicyclic or heterocyclic series. Such ester groups are preferably derived from therapeutically acceptable acids. The aliphatic acids are preferably lower acids with a maximum of 8 carbon atoms, such as acetic, propionic, butyric or valeric acids, for example, isovalerianic (isovaleric) acid or their substituted derivatives such as hydroxy acids, for example, glycolic acid or hydroxybutyric acid, and lactic acid, aminoacids such as natural aminoacids, e.g., glycine, alanine, valine or phenylglycine, or dibasic acids. The dibasic acids may also be substituted, such as malonic acid, succinic acid, maleic acid and malic acid. Those of the aromatic series are, for example, benzoic acid or its derivatives substituted by between 1 and 3 lower alkyl groups, hydroxy groups or lower alkoxy groups, or by halogens, such as chlorine, fluorine or bromine. Of the araliphatic alcohols, special mention should be made of those with only one benzene ring, such as phenylacetic or phenylpropionic acid, optionally substituted as described above. Alicyclic acids are preferably those with rings of 5 or 6 carbon atoms, for example, hexanecarbonic acid or hexanedicarbonic acid. Acids of the heterocyclic series are preferably simple compounds with only one heterocyclic group, such as the derivatives of pyridine or piperidine, e.g., nicotinic or isonicotinic acid or α-pyrrolidinecarbonic acid.

The esterified hydroxy groups may be derived from the alcohols mentioned above in connection with the esterified sialic groups. Preference is given to groups esterified with aliphatic acids having a maximum of 4 carbon atoms or araliphatic alcohols having a maximum of 4 carbon atoms in the aliphatic part and a benzene group optionally substituted as described above.

The substituted amino groups may also be those derived from the amines listed above in connection with the amide groups of sialic acids. Preference is given to amino groups substituted with alkyl groups having a maximum of 4 carbon atoms or aralkyl groups having a maximum of 4 carbon atoms in the aliphatic part and a benzene group optionally substituted as described above. A substituted amino group may also include an acylated amino group, for example, with one of the acids mentioned in connection with the esterified hydroxy groups, particularly having an aliphatic acid with a maximum of 4 carbon atoms.

The lower hydrocarbyl aliphatic or araliphatic groups described herein and concerning the substitution of the keto, aldehyde, aldoxime, mercapto, sulfonic, sulfamide, sulfone and sulfoxide moieties are groups with a maximum of 8 carbon atoms, preferably with 1 to 4 carbon atoms. Hydrazone groups can also be derived from such hydrocarbyl groups, including a phenylhydrazone group.

The esterified carboxy groups as possible polar substitutents on the N-acyl group according to the present invention may be those described above in connection with the esters of the sialic groups of ganglioside derivatives, but they are preferably derived from alcohols of the aliphatic series with a maximum of 8 carbon atoms and especially with 4 carbon atoms. Of the lower saturated acids having the above-said number of carbon atoms, from which the N-acyl group is derived, special mention should be made of the halogenated ones and especially the chlorinated or fluorinated acids, and particularly which are dichlorinated in the 2-position.

Of special note are dichloroacetic acid, trichloroacetic acid and its fluorinated or brominated analogues, 2,2-dichloropropionic acid, 2,3-dichloropropionic acid, 2,2,3-trichloropropionic acid, normal-2,2-dichlorobutyric acid, 2,2-dichlorovalerianic acid, 2-chloroisovalerianic and, 2,3-dichlorovalerianic acid, pentafluoropropionic acid, 3,3-dichloropivalic acid, 3-chloro-2,2-dimethylpropionic acid, chlorodifluoroacetic acid, 2,2-dichlorocaproic acid, 2-monochloropropionic acid, 2-monochloro-normal-butyric acid, 2-monochlorovalerianic acid, 2-monochlorocapronic acid, and the fluorinated or brominated analogues of these acids, 2-chloropalmitic acid, 2-chlorostearic acid, 2-chlorooleic acid, 2-chlorolauric acid, 2-chlorobehenic acid, 4-chlorophenoxyacetic acid, 2-hydroxypropionic acid (lactic acid), 3-hydroxypropionic acid, 2-hydroxybutyric acid, 2-hydroxyvalerianic acid, 3-hydroxyvalerianic acid, 2,3-dihydroxybutyric and 2,3-dihydroxyvalerianic acids or their ethers with lower aliphatic alcohols having a maximum of 4 carbon atoms or esters thereof with the hydroxy groups with lower aliphatic acids having a maximum of 4 carbon atoms, or with one of the above acids of the aromatic, araliphatic, alicyclic or heterocyclic series. Such acids include methoxyacetic acid, 12-hydroxystearic acid, 2-(4-hydroxyphenoxy) propionic acid, 2-hydroxyisocapronic acid, 2-hydroxyisobutyric acid, 4-fluorophenoxyacetic acid, ethoxyacetic acid, pyruvic acid, acetoacetic acid, levulinic acid and their ketals with lower aliphatic alcohols having a maximum of 4 carbon atoms and/or their oximes or substituted oximes with alkyl groups with a maximum of 4 carbon atoms, mercaptoacetic, 2-mercaptopropionic, 2-mercaptobutyric or 2-mercaptovalerianic acids and their ethers with lower aliphatic monovalent alcohols having a maximum of 4 carbon atoms or their esters with lower aliphatic acids with a maximum of 4 carbon atoms. Also of interest are 2-mercapto laurinic acids, oleic and palmitic acids and their esters or ethers of the above-said type, malonic acid, glutaric acid, monomethylglutaric acid, 3-hydroxy-3-methylglutaric acid, maleic acid, malic acid, succinic acid, fumaric acid, azelaic acid and their esters with aliphatic alcohols with a maximum of 4 carbon atoms, sulfoacetic acid, 2-sulfopropionic acid, 2-sulfobutyric acid, 2-sulfovalerianic acid and their esters with aliphatic alcohols with a maximum of 4 carbon atoms. Among the higher acids substituted by sulfonic groups can be mentioned 2-sulfolaurinic acid, 2-sulfooleic acid, 2-sulfopalmitic acid, 2-sulfostearic acid and their esters of the above-said type, as well as the corresponding sulfamides or sulfamides substituted by lower alkyl groups having a maximum of 4 carbon atoms or by alkylene groups having 4 or 5 carbon atoms, acetic, propionic, butyric and valerianic acids substituted in the 2-position by an alkylsulfoxide or alkylsulfone group in which the alkyl has a maximum of 4 carbon atoms, cyanacetic acid, 2-cyanpropionic acid, 2-cyanbutyric acid, 2-cyanvalerianic acid, aminoacetic acid, 2-aminopropionic acid, 2-aminobutyric acid, 3-aminobutyric acid, 4-aminobutyric acid, 2-aminovalerianic acid, 4-aminovalerianic acid and their derivatives with one or two alkyls substituted on the amine hydrogen with a maximum of 4 carbon atoms or with an alkylene group with 4 or 5 carbon atoms, or derivatives of these acids with an acylated amino group with a lower aliphatic acid having between 1 and 4 carbon atoms or with one of the aromatic, alicyclic or heterocyclic acids mentioned above. Such derivatives include quaternary ammonium salts of tertiary amino groups derived from alkyl groups having a maximum of 4 carbon atoms. Other acids include ethionine, dimethylglycine, 3-diethylaminopropionic acid, carnitine and cysteic acid.

It is possible to prepare metal or organic base salts of the N-acyl lysoganglioside compounds according to the present invention having free carboxy functions, and these also form part of the invention. It is possible to prepare metal or organic base salts of other derivatives of the invention too, which have free acid functions, such as esters or peracylated amides with dibasic acids. Also forming part of the invention are acid addition salts of ganglioside derivatives which contain a basic function, such as a free amino function, for example, esters with aminoalcohols. Of the metal or organic base salts particular mention should be made of those which can be used in therapy, such as salts of alkali or alkaline earth metals, for example, salts of potassium, sodium, ammonium, calcium or magnesium, or of aluminum, and also organic base salts, for example of aliphatic or aromatic or heterocyclic primary, secondary or tertiary amines, such as methylamine, ethylamine, propylamine, piperidine, morpholine, ephedrine, furfurylamine, choline, ethylenediamine and aminoethanol. Of those acids which can give acid addition salts of the ganglioside derivatives according to the invention special mention should be made of hydroacids such as hydrochloric acid, hydrobromic acid, phosphoric acid, sulfuric acid, lower aliphatic acids with a maximum of 7 carbon atoms, such as formic, acetic or propionic acids, succinic and maleic acids. Acids or bases which are not therapeutically useful, such as picric acid, can be used for the purification of the ganglioside derivatives of the invention and also form part of the invention.

Due to the close relationship between the derivatives in the free form and in the form of their salts, no particular distinction is made herein between these two forms, unless explicitly stated to the contrary and unless the meaning itself excludes this possibility.

Of the new N-acyl lysogangliosides or their functional derivatives of the present invention special mention should be made of those having an acyl group derived from one of the above-mentioned substituted acids and having as the basic ganglioside one chosen from the group formed by $GM_1$, $GM_3$, GD1a, GD1b, $GT_{1b}$, their sialic esters derived from ethyl, propyl, isopropyl, n-butyl, isobutyl, tert-butyl, benzyl, allyl, ethoxycarbonylmethyl or cyclohexyl alcohols, sialic amides and the amides derived from methylamine, ethylamine, propylamine, dimethylamine, diethylamine, pyrrolidine, piperidine, piperazine, morpholine, thiomorpholine, their peracylates, perpropionylates, perbutyrilates, permaleinylates, permalonylates, persuccinylates and peracylate analogues of said sialic esters and amides. Also to be mentioned are the mixtures of N-acyl lysogangliosides containing mainly those derived from the gangliosides $GM_1$, GD1a, GD1b, $GT_{1b}$, N-acylated with the acids mentioned above, and the same functional derivatives as mentioned above for the derivatives of the single gangliosides. Of particular note are the following N-acyl lysogangliosides: dichloroacetyl lyso $GM_1$, chloroacetyl lyso $GM_1$, 3-chloropivaloyl lyso $GM_1$, hydroxyacetyl lyso $GM_1$, trifluoroacetyl lyso $GM_1$, trichloroacetyl lyso $GM_1$, tribromoacetyl lyso $GM_1$, mercaptoacetyl lyso $GM_1$, maleyl lyso $GM_1$, 12-hydroxystearoyl lyso $GM_1$, 2-hydroxyisobutyroyl lyso $GM_1$, fluoroacetyl lyso $GM_1$, difluoroacetyl lyso $GM_1$, 3-aminopropionyl lyso $GM_1$, cyanoacetyl lyso $GM_1$, 3-diethylaminopropionyl lyso $GM_1$, aminoacetyl lyso $GM_1$, and the esters and amides and peracylates analogous to those mentioned above.

The new lysoganglioside derivatives of the present invention may be prepared in the known way. It is possible to selectively deacylate gangliosides at the sphingosine nitrogen with appropriate enzymes, directly obtaining lysogangliosides which maintain the other acyl groups present intact, especially those on the amino group of neuraminic acid. By acylating in the known way it is then possible to obtain N-acyl-lysogangliosides.

Alternatively, the gangliosides can be deacylated chemically, thus obtaining de-N-acetyl-lysogangliosides, that is, compounds in which the amino groups of sphingosine and neuraminic acids are deacylated, and possibly with esterified hydroxy groups. These products can be acylated in the known way, thus obtaining de-N-acetyl-N-acyl-lysogangliosides. These can then be acetylated to the amino group of neuraminic acid.

A variation of this procedure is to proceed to effect an intermediate provisional protection of the sphingosine amino group, which can be done, for example, by means of hydrophobic interaction with phosphatidylcholine or by acylation with protective groups, subsequent acetylation on the nitrogen of neuroaminic acid and optionally deprotection of sphingosine nitrogen and lastly, N-acylation on sphingosine nitrogen. All of these operations can also be effected on the described ganglioside mixtures.

In N-acyl-lysogangliosides it is possible, if desired, to functionally convert the carboxy groups of the sialic acids or the hydroxyls of such acids, for example to convert the carboxyls into esters or amides or the hydroxyls into their esterified groups with acids (peracylation). It is possible, on the other hand, either before, simultaneously or after these functional conversions, to convert, either functionally or not, polar groups present in the acyl group of the ceramide residue, for example to esterify hydroxy groups, or to alkylate amino groups, or to react carbonyl groups with O-alkyl hydroxylamine. It is also possible to convert the compounds obtained into their salts.

The procedure of the present invention therefore consists in acylating a lysoganglioside or a de-N-acetyl-lysoganglioside, or mixtures of these compounds, optionally following temporary protection of the free functional groups in the acylating component, with an aliphatic acid having between 2 and 24 carbon atoms, substituted by one or more polar groups chosen from:

chlorine, bromine and fluorine;

free hydroxy groups or hydroxy groups esterified with an organic or inorganic acid;

etherified hydroxy groups;

keto, ketal and acetal groups derived from lower aliphatic or araliphatic alcohols;

ketoxime, aldoxime or hydrazone groups optionally substituted by lower alkyl or aralkyl groups;

free mercapto groups or mereapto groups esterified with a lower aliphatic or araliphatic acid or etherified with lower aliphatic or araliphatic alcohols;

free or esterified carboxy groups;

free sulfonic acid groups or sulfonic groups esterified with lower aliphatic or araliphatic alcohols;

sulfamide or sulfamidic groups substituted by lower alkyl or aralkyl groups or lower alkylene groups;

sulfoxide or sulfone groups derived from lower alkyl or aralkyl groups;

nitrile groups;

free or substituted amino groups, and quaternary ammonium derivatives of such amino groups.

The procedure of the invention also comprises acetylating the de-N-acetyl-N-acyl-lysoganglioside thus obtained, or the mixture of compounds of this type and, if desired, converting the N-acyl-lysoganglioside obtained into esters or amides or into inner esters or into hydroxy peracylates, or a mixture of compounds of this type, and/or optionally converting the polar groups substituted on the N-acyl group between each other and, if desired, converting the products obtained into suitable salts. N-acylation according to the described procedure can be carried out in the conventional way, for example, by reacting the starting products with an acylating agent, particularly with a reactive functional derivative of the acid, whose residue is to be introduced. Thus, it is possible to use as the functional derivative of the acid, a halogenide or an anhydride, and acylation is effected preferably in the presence of a tertiary base, such as pyridine or collidine. Operations can be carried out under anhydrous conditions, at room temperature or by heating or also, to advantage, according to the Schotten-Baumann method under aqueous conditions in the presence of an inorganic base. In some cases it is also possible to use the esters of the acids as reactive functional derivatives. For acylation it is possible to also use methods involving activated carboxy derivatives, such as are known in peptide chemistry, for example using mixed anhydrides or derivatives obtainable with carbodiimides or isoxazole salts.

Of the numerous preparation methods, the most appropriate are the following:

1. reaction of the lysoganglioside derivative with the azide of the acid;
2. reaction of the lysoganglioside derivative with an acylimidazole of the acid obtainable from the acid with N,N'-carbonyldiimidazole;
3. reaction of the lysoganglioside derivative with a mixed anhydride of the acid and of trifluoro-acetic acid;
4. reaction of the lysoganglioside derivative with the chloride of the acid;
5. reaction of the lysoganglioside derivative with the acid in the presence of a carbodiimide (such as dicyclohexylcarbodiimide) and optionally of a substance such as 1-hydroxybenzotriazol;
6. reaction of the lysoganglioside derivative with the acid by heating;
7. reaction of the lysoganglioside derivative with a methyl ester of the acid at a high temperature;
8. reaction of the lysoganglioside derivative with a phenol ester of the acid, such as an ester with para-nitrophenol; and
9. reaction of the lysoganglioside derivative with an ester derived from the exchange between a salt of the acid and 1-methyl-2-chloropyridine iodide or similar products.

In the particular case of the preparation of the products derived from acids containing free hydroxy or mercapto or carboxy groups, or primary or secondary amino groups, it is preferable to protect such groups during the acylation reaction, using preferably those protection methods which are used in peptide chemistry. Such protective groups should naturally be easily eliminated at the end of the reaction, such as the phthaloyl group or the benzyloxycarbonyl group, which serves to advantage for the protection of the amino group. Thus, for example, in the preparation of derivatives containing Γ-amino butyric acid, a derivative, of this acid is first prepared, where the amino group is bound to the phthaloyl group, and after acylation with the lysoganglioside derivative the phthaloyl group is eliminated by hydrazinolysis. The benzyloxycarbonyl group can be eliminated by hydrogenolysis. This residue may also serve for the protection of the hydroxy groups. The carboxy group can be protected by esterification, for example, with the alcohols used in peptide chemistry.

The starting lysogangliosides can be obtained, as already indicated, from gangliosides by enzymatic deacylation on the nitrogen with an enzyme called ceramide deacylase. This method is described for example in J. Biochem. 103, 1 (1988). The de-N-acetyl-lysogangliosides which can also be used as starting products are obtainable from gangliosides with alkaline hydrolyzing agents, for example hydroxides of tetraalkylammonium, potassium hydrate and others [see Biochemistry 24, 525, (1985); J. Biol. Chem. 255, 7657, (1980); Biol. Chem. Hoppe Seyler 367, 241 (1986); Carbohydr. Res. 179, 393 (1988); Bioch. Bioph. Res. Comm. 147, 127 (1987)].

De-N-acetyl-lysogangliosides, as well as being starting materials in a variation of the described procedure, can also constitute starting materials for the preparation of the starting materials in another variation, that is, for the preparation of lysogangliosides. As can be seen from Table 4, this conversion can be effected according to parts (3) and (4) thereof. Reactions (a) and (b) of method (3) and (a), (b) and (c) of method (4) are already known. It is possible to prepare carboxy or hydroxy derivatives of the new N-acyl-lysogangliosides obtained according to this procedure according to methods which are already known, with the exception of those methods which would have the effect of altering the basic ganglioside structure, such as those employing highly acidic agents or which are effected in highly alkaline or acid conditions, or also those methods which would lead to undesired alkylation of the hydroxy groups of the saccharide part.

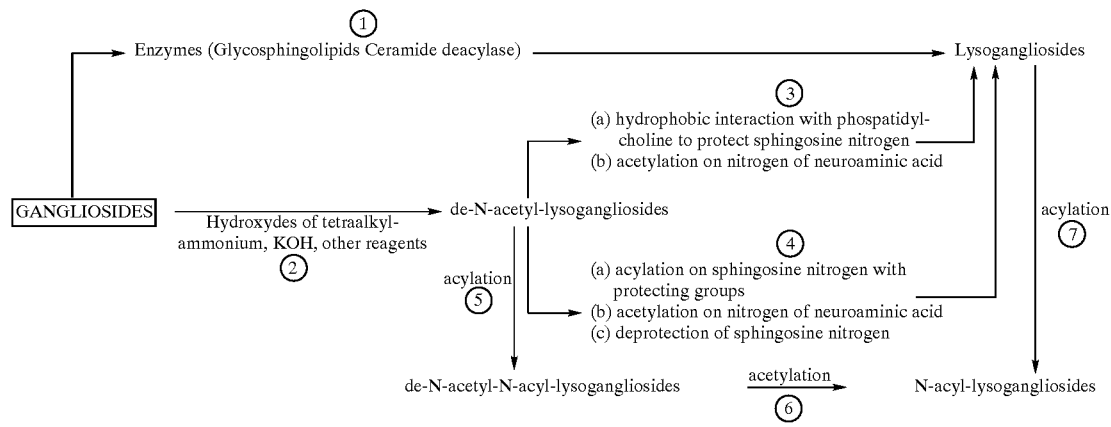

Esterification of the carboxy groups of N-acyl gangliosides or their conversion into amides can be effected for example as described in U.S. Pat. No. 4,713,374 for gangliosides. The formation of inner esters of the derivatives of the invention may also be effected in the same way as in the preparation of inner esters of gangliosides, as described for example in U.S. Pat. No. 4,593,091 and EPO patent No. EP 0072 722. These inner esters not only include the compounds formed by lactonization of sialic carboxy groups with hydroxy saccharides, but also for example those which contain lactone rings formed between the sialic carboxyls and the sialic hydroxyls, these latter being in turn bound to the saccharide part, and also other possible lactone structures. The procedure described in said patents for the formation of inner esters comprises treating a ganglioside in a nonaqueous organic solvent under anhydrous conditions with a lactonizing agent. Suitable organic solvents include dimethylsulfoxide, dimethylformamide, sulfolane, tetrahydrofuran, dimethoxyethane, pyridine or mixtures of these solvents. Suitable lactonizing agents include carbodiimides soluble in organic solvents, such as dicyclohexylcarbodiimide, benzylisopropylcarbodiimide, benzylethylcarbodiimide, 2-chloro-1-methylpyridine salts, ethoxyacetylene and Woodward's reagent (N-ethyl-5-phenylisoxazole-3'-sulfonate). Older methods involve the reaction between a ganglioside and acetic or trichloroacetic acid or with a carbodiimide soluble in water or in an aqueous medium. All of these methods can be used for the preparation of inner esters of the new N-acyl-lysogangliosides.

For the "outer" esterification of carboxy groups, that is, the esterification with alcohols of the above-said series, it is possible for example to react the N-acyl lysogangliosides with the desired alcohol, in the presence of an ion exchanger, such as a Dowex 50, the yield being limited due to the simultaneous formation of inner esters and the reaction times which are quite long. Another esterification method involves passing the alcohol over a resin such as Dowex-50Wx8 (100–200 mesh form H) and treating the dissolved eluate in the same alcohol with the corresponding diazoalkane. Another suitable preparation method for esters comprises treating a metal salt of the lysoganglioside derivative with an etherifying agent. Alkali metal salts are used, or alkaline earth salts or also any other metal salt. As etherifying agent it is possible to use those reported in the literature, especially the esters of various inorganic acids, or organic sulfonic acids, such as hydracids, that is, in other words, hydrocarbyl halogenides, such as methyl or ethyl iodides etc., or neutral sulfates or hydrocarbyl acids, sulfites, carbonates, silicates, phosphites or hydrocarbyl sulfonates, such as benzo- or p-toluolsulfonate. Reaction can be effected in a suitable solvent, for example an alcohol, preferably that corresponding to the alkyl groups to be introduced, but also in nonpolar solvents, such as ketones, ethers such as dioxane or dimethylsulfoxide. One particularly advantageous method of esterification comprises treating an inner ester of the lysoganglioside derivative with a mixture of the desired alcohol and its corresponding alcoholate. Reaction can be conducted at a temperature corresponding to the boiling point of the alcohol, but it can also be effected at a lower temperature, where the reaction times would be longer.

The amides of the lysoganglioside derivatives of the present invention can be prepared by the known methods, and especially by the following methods:

a) reaction of the inner esters of N-acyl lysoganglioside derivatives with ammonia or amines;

b) reaction of the carboxy esters of N-acyl lysoganglioside derivatives with ammonia or amines;

c) reaction of N-acyl lysoganglioside derivatives with activated carboxy groups with ammonia or amines;

Reaction (a) can be effected by direct treatment, with or without solvent, of the ganglioside inner ester with ammonia or with an amine whose amide is to be prepared. The reaction can be effected also at quite low temperatures, such as for example between −5 and +10°, but preferably at room temperature or over, for example between 30 and 120°. As solvents it is possible to use ketones, aromatic hydrocarbons, dimethylformamide, dimethylsulfoxide, dioxane or tetrahydrofuran. Reaction (b) should also be effected preferably under the conditions described for (a).

As well as the esters described for the present invention, it is also possible to use other esters, for example esters with phenols. For the activation of the carboxy groups in the reaction according to method (c), those methods known in peptide chemistry should be used, avoiding however those methods which require too acidic or too basic conditions which would lead to the disintegration of the ganglioside molecule. If the starting gangliosides are in the form, for example, of sodium salts, it is advisable first to treat the salt with a Dowex-type ion exchanger or another acid ion exchanger. For instance, it is possible to use the condensation method in the presence of carbodiimides, for example dicyclohexylcarbodiimide, benzylisopropylcarbodiimide or benzylethylcarbodiimide, in the presence of 1-hydroxybenzotriazole or condensation in the presence of N,N'-carbonyldiimidazole.

Acylation of the carboxy groups of the saccharide or sialic part and optionally of the ceramide residue can be effected in the known way, for example by acylation with a halogenide or an anhydride of the acid to be used for acylation, preferably in the presence of a tertiary base, such as pyridine or collidine. The peracylated derivatives are thus obtained.

It is also possible, according to the definition of the procedure of the present invention, to submit to acylation a de-N-acetyl-lysoganglioside and to restore the acetylamino group in the neuraminic acid after acylation. Such acetylation can also be effected in the known way. In this case relatively mild methods are chosen for N-acylation, in which the hydroxy group of the neuraminic acid remains unchanged. Acetylation of this group, to be effected after acylation reaction on the sphingosine nitrogen, can be effected using drastic methods, especially with the use of acetic anhydride. In the compounds obtained according to this procedure, it is possible, if desired, to convert the functions present in the N-acyl group between each other. For example, it is possible to acylate the hydroxy groups selectively, leaving intact other hydroxy groups, such as sialic groups, using mild reagents and conditions.

It is possible to etherify the hydroxy or mercapto groups or to alkylate the amino groups or the acylated amino groups. Finally, in all of the compounds obtainable according to the procedures which present salifiable groups, such groups can be salified in the known way.

The invention also includes modifications of the preparation procedure of the new derivatives, in which a procedure is interrupted at any one stage, or in which an intermediate compound is used to start with and the remaining stages are carried out, or in which the starting products are formed in situ.

Another object of the present invention concerns the pharmaceutical preparations which include as the active substance one or more of the new N-acyl-lysoganglioside derivatives and particularly those already described above. The pharmaceutical preparations may be preparations for oral, rectal, parenteral, local or transdermal use. They are therefore in the form of solids or semisolids, for example pills, tablets, gelatin capsules, capsules, suppositories or soft gelatin capsules. For parenteral use, those forms intended for intramuscular, subcutaneous or transdermal administration can be used, or those suitable for infusion or intravenous injection. These preparations can therefore be in the form of solutions of the active compounds or freeze-dried powders of the active compounds to be mixed with one or more pharmaceutically acceptable excipients or diluents, suitable for said uses and with an osmolarity which is compatible with the physiological fluids. For local use preparations in the form of sprays should be considered, for example nasal sprays, creams or ointments for topical use or specially prepared sticking plasters for transdermal administration.

The preparations of the invention are suitable for administration to both man and animals. They contain preferably between 0.01% and 10% by weight of active compound in the case of solutions, sprays, ointments and creams and between 1% and 100% by weight, and preferably between 5% and 50% by weight, of active compound in the case of solid form preparations. Doses to be administered will depend on individual needs, on the desired effect and on the chosen route of administration. Daily doses for administration by injection of the new N-acyl-lysogangliosides to man (subcutaneous or intramuscular routes) or by transdermal or oral routes, vary between 0.05 mg and 5 mg of active substance per kg of body weight.

The following Examples 3–16 and 18–32 illustrate the preparation of the new derivatives according to the invention and Examples 33–34 illustrate the pharmaceutical preparations. Examples 1, 2 and 17 illustrate the preparation of some starting substances necessary for the procedure of the invention.

EXAMPLE 1 de-N-acetyl Lyso $GM_1$ 10 g of $GM_1$ are dissolved in 200 ml KOH 3N and hydrolysis reaction is conducted for 72 hrs at 90° C. The solution is then cooled and brought to pH 6.5 with hydrochloric acid. It is left to rest for 18 hrs at 4° C. and then the precipitated fatty acids are eliminated by filtration. It is dialyzed against water and concentrated to 500 ml and precipitated in 5 liters of diacetone.

The product is dried and then high resolution silica gel chromatography is effected using as eluent a mixture of chloroform/methanol/$NH_3$ 5N (55:45:10). The fractions containing the product are dried and then redissolved in water. It is brought to pH 10 with NaOH 0.01 N and dialysed, concentrated to 100 mg/ml and precipitated in 5 volumes of acetone.

Yield of de-N-acetyl-lyso $GM_1$ 5.7 g (70% theoretical).

Silica gel chromatography, using as solvent a mixture of chloroform/methanol/$NH_3$ 5N (55:45:10) shows the product to be a unitary compound with Rf=0.05 ($GM_1$=0.35)

EXAMPLE 2

Lyso $GM_1$ 10 g (6.37 mM) of $GM_1$ are dissolved in 200 ml KOH 3N and hydrolysis reaction is conducted for 72 hrs at 90° C.

The solution is then cooled and brought to pH 6.5 with hydrochloric acid. It is left to rest for 18 hrs at 4° C. and then the precipitated fatty acids are eliminated by filtration. It is dialysed against water and concentrated to 500 ml and precipitated in 5 liters of acetone.

The product containing de-N-acetyl-lysogangliosides and de-N-acetyl-gangliosides (20%) is vacuum dried and then redissolved in 100 ml of dimethylformamide. To this are slowly added 2.15 g (6.37 mM) of 9-fluorenylmethyloxycarbonyl-N-hydroxysuccinimide dissolved in 20 ml of tetrahydrofuran and it is left to react for 1 hr at room temperature. Finally, 3 ml (31.85 mM) of acetic anhydride and 0.9 ml (63.7 mM) of triethylamine are added. 30 minutes later 12.5 ml of piperidine are added to remove the protector group. It is left to react for 18 hrs at room temperature and precipitated in 2 liters of acetone and dried. The material thus obtained is dissolved in $Na_2CO_3$ 1M and kept at 60° C. for 1 hr. It is dialysed, concentrated to 100 mg/ml and precipitated in 5 volumes of acetone.

The product, constituted by Lyso $GM_1$ (70%) and by de-N-acetyl lyso $GM_1$, is passed on an S. Sepharose column (H+ form) equilibrated in methanol. It is eluted with methanol and Lyso $GM_1$ is obtained, eluting with $NH_4Cl$ 10 mM in methanol.

The fractions containing the product are dried and then redissolved in water. They are brought to pH 10 with NaOH 0.01N and dialysed, concentrated to 100 mg/ml and precipitated in 5 volumes of acetone.

Product obtained: approximately 5 g (theoretical 60%).

Silica gel chromatography, using as solvent a mixture of chloroform/methanol/$NH_3$ 5N (55:45:10) shows the product to be unitary with Rf=0.11.

EXAMPLE 3

N-dichloroacetyl Lyso $GM_1$ 500 mg (0.38 mM) of Lyso $GM_1$ (prepared according to Example 2) are dissolved in 1 ml of dimethylformamide/methanol 1:1, at 0° C., and 528 µl (3.8 mM) of triethylamine and 579 µl (3.8 mM) of dichloroacetic anhydride are added and left to react at room temperature for 72 hrs. It is precipitated in 20 volumes of ethyl acetate, filtered and dried.

The product is then purified by silica gel chromatography, using as eluent a mixture of chloroform/methanol/water (60:35:8).

The pure fractions are reunited, evaporated, gathered with $Na_2Co_3$ 1N, dialysed against distilled water and then concentrated to 5 ml and precipitated in 50 ml diacetone.

Product obtained: 423 mg (78.0% theoretical).

Silica gel chromatography, using as solvent a mixture of chloroform/methanol/$CaCl_2$ 0.2% (50:42:11), shows the product to be a unitary compound with Rf=0.35 ($GM_1$=0.43; Lyso $GM_1$=0.24).

EXAMPLE 4

N-Monochloroacetyl Lyso $GM_1$ 500 mg (0.38 mM) of Lyso $GM_1$ (prepared according to Example 2) are dissolved in 1 ml of dimethylformamide/methanol 1:1 and at a temperature of 0° C. are added 528 µl (3.8 mM) of triethylamine and 649.7 mg (3.8 mM) of monochloroacetic anhydride, and the mixture is left to react at room temperature for 72 hrs. It is precipitated in 20 volumes of ethyl acetate, filtered and dried.

The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 391 mg (74.0% theoretical).

Silica gel chromatography, using as solvent a mixture of chloroform/methanol/$CaCl_2$ 0.2% (50:42:11), shows the product to be a unitary compound with Rf=0.30 ($GM_1$=0.43; Lyso $GM_1$=0.24).

EXAMPLE 5

N-Monofluoroacetyl Lyso $GM_1$ 500 mg (0.38 mM) of Lyso $GM_1$ (prepared according to Example 2) are dissolved in 2.5 ml of dimethylformamide and to this are added 528 µl (3.8 mM) of triethylamine, 193 mg (3.8 mM) of fluoracetic acid sodium salt and 194.2 mg (0.76 mM) of 1-methyl-2-chloropyridine iodide dissolved in 2.5 ml of dimethylformamide.

It is left to react for 18 hrs at room temperature and then precipitated in 50 ml of ethyl acetate saturated with water. It is dried and silica gel chromatography is effected, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 481 mg (92% theoretical).

Silica gel chromatography, using as solvent a mixture of chloroform/methanol/$CaCl_2$ 0.3% (50:42:11), shows the product to be a unitary compound with Rf=0.33 ($GM_1$=0.43; Lyso $GM_1$=0.24).

EXAMPLE 6

N-difluoroacetyl Lyso $GM_1$ 500 mg (0.38 mM) of Lyso $GM_1$ (prepared according to Example 2) are dissolved in 2.5 ml of dimethylformamide and to this are added 528 μl (3.8 mM) of triethylamine, 243 μl (3.8 mM) of difluoracetic acid and 194.2 mg (0.76 mM) of 1-methyl-2-chloropyridine iodide dissolved in 2.5 ml of dimethylformamide.

It is left to react for 18 hrs at room temperature and then precipitated in 50 ml of ethyl acetate saturated with water. It is dried and silica gel chromatography is effected, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 365 mg (84% theoretical).

Silica gel chromatography, using as solvent a mixture of chloroform/methanol/$CaCl_2$ 0.3% (50:42:11), shows the product to be a unitary compound with Rf=0.35 ($GM_1$=0.43; Lyso $GM_1$=0.24).

EXAMPLE 7

N-methoxyacetyl Lyso $GM_1$ 500 mg (0.38 mM) of Lyso $GM_1$ (prepared according to Example 2) are dissolved in 2.5 ml of dimethylformamide and to this are added 161 μl (1.14 mM) of triethylamine, 293 μl (3.8 mM) of methoxyacetic acid and 194.2 mg (0.76 mM) of 1-methyl-2-chloropyridine iodide dissolved in 2.5 ml of dimethylformamide.

It is left to react for 18 hrs at room temperature and then precipitated in 50 ml of ethyl acetate saturated with water. It is dried and silica gel chromatography is effected, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 325 mg (74% theoretical).

Silica gel chromatography, using as solvent a mixture of chloroform/methanol/$CaCl_2$ 0.3% (50:42:11), shows the product to be a unitary compound with Rf=0.36 ($GM_1$=0.43; Lyso $GM_1$=0.24).

EXAMPLE 8

N-(3-diethylaminopropionyl) Lyso $GM_1$ 500 mg (0.38 mM) of Lyso $GM_1$ (prepared according to Example 2) are dissolved in 2.5 ml of dimethylformamide and to this are added at room temperature 528 μl (3.8 mM) of triethylamine, 350 mg (1.9 mM) of 3-diethylaminopropionic acid and 194.2 mg (0.76 mM) of 1-methyl-2-chloropyridine iodide dissolved in 2.5 ml of dimethylformamide.

The mixture is left to react for 18 hrs at room temperature and then precipitated in 100 ml of acetone. It is filtered and dried. The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 411 mg (75% theoretical).

Silica gel chromatography, using as solvent a mixture of chloroform/methanol/$CaCl_2$ 0.3% (50:42:11), shows the product to be a unitary compound with Rf=0.22 ($GM_1$=0.43; Lyso $GM_1$=0.24).

EXAMPLE 9

N-trifluoroacetyl Lyso $GM_1$ 500 mg (0.38 mM) of Lyso $GM_1$ (prepared according to Example 2) are dissolved in 1 ml of dimethylformamide/methanol 1:1 and to this are added, at 0° C., 161 μl (1.14 mM) of triethylamine and 161 μl (1.14 mM) of trifluoroacetic anhydride, and the mixture is left to react at room temperature for 72 hrs. It is precipitated in 20 volumes of ethyl acetate, filtered and dried.

The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 292 mg (55.0% theoretical).

Silica gel chromatography, using as solvent a mixture of chloroform/methanol/$CaCl_2$ 0.3% (50:42:11), shows the product to be a unitary compound with Rf=0.37 ($GM_1$=0.43; Lyso $GM_1$=0.24).

EXAMPLE 10

N-trichloroacetyl Lyso $GM_1$ 500 mg (0.38 mM) of Lyso $GM_1$ (prepared according to Example 2) are dissolved in 1 ml of dimethylformamide/methanol 1:1 and to this are added, at 0° C., 528 μl (3.8 mM) of triethylamine and 352 mg (1.14 mM) of trichloroacetic anhydride, and the mixture is left to react at room temperature for 72 hrs. It is precipitated in 20 volumes of ethyl acetate, filtered and dried.

The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 358 mg (65.0% theoretical).

Silica gel chromatography, using as solvent a mixture of chloroform/methanol/$CaCl_2$ 0.3% (50:42:11), shows the product to be a unitary compound with Rf=0.37 ($GM_1$=0.43; Lyso $GM_1$=0.24).

EXAMPLE 11

N-cyanoacetyl Lyso $GM_1$ 500 mg (0.38 mM) of Lyso $GM_1$ (prepared according to Example 2) are dissolved in 2.5 ml of dimethylformamide and to this are added, at 0° C., 106 µl (0.76 mM) of triethylamine and cyanoacetic anhydride prepared immediately before use by reacting 620 mg (7.6 mM) of cyanoacetic acid and 939 mg (9.12 mM) of dicyclohexylcarbodiimide dissolved in 20 ml of tetrahydrofuran, and 2 hrs later by filtering the dicyclohexylurea which is formed.

A condensation reaction is conducted at 0° C. for 18 hrs under agitation. Once reaction is complete, the solution is concentrated to 1 ml, precipitated in 10 ml of acetone and vacuum dried.

The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 273 mg (52% theoretical).

Silica gel chromatography, using as solvent a mixture of chloroform/methanol/$CaCl_2$ 0.3% (50:42:11), shows the product to be a unitary compound with Rf=0.40 ($GM_1$=0.43; Lyso $GM_1$=0.24).

EXAMPLE 12

N-maleyl Lyso $GM_1$ 500 mg (0.38 mM) of Lyso $GM_1$ (prepared according to Example 2) are dissolved in 1 ml of dimethylformamide and to this are added 53.6 µl (0.38 mM) of triethylamine and 37 mg (0.38 mM) of maleic anhydride and left to react at room temperature for 72 hrs. It is precipitated in 20 volumes of ethyl acetate, filtered and dried.

The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 25 ml of acetone.

Product obtained: 492 mg (85% theoretical).

Silica gel chromatography, using as solvent chloroform/methanol/$CaCl_2$ 0.3% (50:42:11), shows the product to be a unitary compound with Rf=0.27 ($GM_1$=0.43; Lyso $GM_1$=0.24).

EXAMPLE 13

N-hydroxyacetyl Lyso $GM_1$ 500 mg (0.38 mM) of Lyso $GM_1$ (prepared according to Example 2) are dissolved in 2.5 ml of dimethylformamide and to this are added, at 0° C., 106 µl (1.14 mM) of triethylamine and glycolic anhydride prepared immediately before use by reacting 173 mg (2.28 mM) of glycolic acid and 939 mg (9.12 mM) of dicyclohexylcarbodiimide dissolved in 20 ml of tetrahydrofuran, and by filtering 2 hrs later the dicyclohexylurea which is formed.

The condensation reaction is conducted at 0° C. for 18 hrs under agitation. Once reaction is complete, the solution is concentrated to 1 ml, precipitated in 10 ml of acetone and vacuum dried.

The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone Product obtained: 261 mg (50% theoretical)..

Silica gel chromatography, using as solvent a mixture of chloroform/methanol/$CaCl_2$ 0.3% (50:42:11), shows the product to be a unitary compound with Rf=0.33 ($GM_1$=0.43; Lyso $GM_1$=0.24).

EXAMPLE 14

N-tribromoacetyl Lyso $GM_1$ 500 mg (0.38 mM) of Lyso $GM_1$ (prepared according to Example 2) are dissolved in 2.5 ml of dimethylformamide/methanol 1:1 and to this are added, at 0° C., 528 µl (3.8 mM) of triethylamine and tribromo-acetic anhydride prepared immediately before use by reacting 2.25 g (7.6 mM) of tribromoacetic acid and 939 mg (9.12 mM) of dicyclohexylcarbodiimide dissolved in 20 ml of tetrahydrofuran, and by filtering 2 hrs later the dicyclohexylurea which is formed.

The condensation reaction is conducted at 0° C. for 18 hrs under agitation. Once reaction is complete the solution is concentrated to 1 ml, precipitated in 10 ml of acetone and vacuum dried.

The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 267 mg (44% theoretical).

Silica gel chromatography, using as solvent a mixture of chloroform/methanol/$CaCl_2$ 0.3% (50:42:11), shows the product to be a unitary compound with Rf=0.37 ($GM_1$=0.43; Lyso $GM_1$=0.24).

EXAMPLE 15

N-(12-hydroxystearoyl) Lyso $GM_1$ 500 mg (0.37 mM) of de-N-acetyl lyso $GM_1$ (prepared according to Example 1) are dissolved in 5 ml of dimethylformamide and to this are added 1 ml of Triton×100 and 104 µl (0.75 mM) of triethylamine. It is left under agitation until a clear solution is obtained. To this are then added 25 ml of tetrahydrofuran containing 598 mg (1.5 mM) of the ester of N-hydroxysuccinimide with 12-hydroxystearic acid prepared by reacting, for 18 hrs at room temperature, 870 mg of hydroxystearic acid dissolved in 15 ml of anhydrous tetrahydrofuran with 10.5 mg of di(N-succinimidyl) carbonate and 550 µl of triethylamine in 40 ml of acetone.

Reaction is carried out for 24 hrs at room temperature and finally the solution is concentrated and repeatedly precipitated in ethyl acetate.

The raw product is purified by silica gel chromatography, using as solvent a mixture of chloroform/methanol/water (60:30:6).

The intermediate de-$N_1$-acetyl-$N_2$-(12-hydroxystearoyl) lyso $GM_1$ thus obtained is then N-acetylated with acetic anhydride dissolved in chloroform/methanol 1:1 with a molar ratio of 1:1:1.

Once reaction is complete, the product is dried, gathered with 2 ml of chloroform/methanol 1:1 and precipitated in 10 ml of acetone.

The product is then purified by further silica gel chromatography, using as solvent a mixture of chloroform/methanol/water (60:35:8). The pure fractions are reunited, evaporated, gathered with $Na_2CO_3$ 1N, dialysed against distilled water, concentrated to 5 ml and precipitated in 50 ml of acetone.

Yield of N-(12-hydroxystearoyl) lyso $GM_1$=217 mg (34.5% theoretical).

Silica gel chromatography, using as solvent a mixture of chloroform/methanol/calcium chloride 0.3%, (60:35:8), showed the product to be a unitary compound with Rf=0.39 (de-N-acetyl lyso $GM_1$ 0.05, de-N-acetyl $GM_1$ 0.20, $GM_1$ 0.40).

EXAMPLE 16

N-(3-chloropivaloyl) Lyso $GM_1$ 500 mg (0.38 mM) of Lyso $GM_1$ (prepared according to Example 2) are dissolved in 1 ml of dimethylformamide/methanol 1:1 and to this are added, at room temperature, 1.160 µl (7.6 mM) of triethylamine and 990 µl (7.6 mM) of 3-chloropivaloyl chloride.

The condensation reaction is conducted at room temperature for 4 hrs. Once reaction is complete, the solution is precipitated in 10 ml of ethyl-acetate saturated with water, filtered and vacuum dried.

The product is then purified by silica gel chromatography, using as eluent a mixture of chloroform/methanol/water (60:35:8).

The pure fractions are reunited, evaporated, gathered with $Na_2CO_3$ 1N, dialysed against distilled water and then concentrated to 5 ml and precipitated in 50 ml of acetone.

Product obtained: 404 mg (74% theoretical).

Silica gel chromatography, using as solvent a mixture of chloroform/methanol/$CaCl_2$ 0.3% (50:42:11), shows the product to be a unitary compound with Rf=0.33 ($GM_1$=0.43; Lyso $GM_1$=0.24).

EXAMPLE 17

Preparation of a Ganglioside Mixture (GA) by Extraction from Bovine Brain Tissue A quantity of bovine brain cortex, removed from the animal, is homogenized in phosphate buffer at pH 6.8; 6 volumes of tetrahydrofuran are then added and the resulting mixture is centrifuged. The supernatant is re-extracted twice with tetrahydrofuran. After centrifugation the non-polar materials are removed by partitioning with ethyl ether and the aqueous-tetrahydrofuran phase is introduced in an ion exchange column, equilibrated with 50% ethanol. Barium hydroxide is added to the effluent from the column, together with four volumes of ice-cold ethanol. After 18 hours under cold conditions, a precipitate is gathered which is then lightly acidified with hydrochloric acid after being dissolved in water. The solution thus obtained is dialysed and freeze-dried. The yield at this point is approximately 0.6 mg of a mixture of raw gangliosides per gram of nerve tissue used. The freeze-dried powder is dispersed in 20 volumes of chloroform-methanol 2:1. Once the solution obtained has been filtered to make it perfectly clear, it is partitioned by adding 0.2 volumes of a solution of potassium chloride in water at 0.88%. The upper phase is separated, dialysed and freeze-dried. The final yield is approximately 0.3 mg of purified mixture of ganglioside salts per gram of brain tissue. The ganglioside mixture obtained can be fractionated in various portions representing in substance pure gangliosides (as described above), using columns of silicic acid and eluting with mixtures of methanol-chloroform. On average, the resulting composition is approximately 40% of ganglioside $G_{Da1}$, 21% of ganglioside $G_{M1}$, 19% of ganglioside $G_{T1b}$ and 16% of ganglioside $G_{D1b}$.

EXAMPLE 18

N-dichloroacetyl Derivatives of a Mixture of Lysogangliosides

1) Preparation of lysogangliosides 10 g of the ganglioside mixture obtained according to Example 17 is dissolved in 200 ml of KOH 3N and hydrolysis reaction is conducted for 72 hrs at 90° C. The solution is then cooled and brought to pH 6.5 with hydrochloric acid. It is left to rest for 18 hrs at 4° C. and then the precipitated fatty acids are eliminated by filtration. It is dialyzed against water and concentrated to 500 ml and precipitated in 5 liters of acetone.

The product containing de-N-acetyl-lysogangliosides and de-N-acetyl-gangliosides (20%) is vacuum dried and then redissolved in 100 ml of dimethylformamide. To this are then slowly added 2.15 g (6.37 mM) of 9-fluoreneylmethyloxycarbonyl-N-hydroxysuccinimide dissolved in 20 ml of tetrahydrofuran and the whole is left to react for 1 hr at room temperature. Finally, to this are added 3 ml (31.85 mM) of acetic anhydride and 0.9 ml (63.7 mM) of triethylamine. After 30 min, 12.5 ml of piperidine are added to remove the protector group. It is left to react for 18 hrs at room temperature and precipitated in 2 liters of acetone and dried. The material thus obtained is dissolved in $Na_2CO_3$ 1M and kept at 60° for 1 hr. It is dialysed, concentrated to 100 mg/ml and precipitated in 5 volumes of acetone.

The product constituted by lysogangliosides (70%) and de-N-acetyl-lysogangliosides is passed on a column of S-Sepharose (H+ form) equilibrated in methanol. The de-N-acetyl-lysogangliosides are eluted with methanol and the lysogangliosides by eluting with $NH_4Cl$ 10 mM in methanol.

The fractions containing the product are dried and then redissolved in water. It is brought to pH 10 with NaOH 0.01N and dialysed, concentrated to 100 mg/ml and precipitated in 5 volumes of acetone.

Product obtained: 4.7 g (55% theoretical).

2) Preparation of dichloroacetyl derivative 500 mg (0.31 mM) of a previously prepared lysoganglioside mixture are dissolved in 1 ml of dimethylformamide/methanol 1:1 and, at a temperature of 0° C., are added 430 µl (3.1 mM) of triethylamine and 472 µl (3.1 mM) of dichloroacetic anhydride. The whole is then filtered and dried.

The acylated product is separated from the unreacted compound by chromatography on an S-Sepharose (H+ form) column, equilibrated in methanol. The dichloroacetyl derivative is eluted in methanol, dried, gathered with $Na_2CO_3$ 1N, dialysed, concentrated to 2.5 ml and precipitated in 25 ml of acetone.

Product obtained: 345 mg (64% theoretical).

EXAMPLE 19

Methyl Ester of N-methoxyacetyl Lyso $GM_1$ 500 mg (0.36 mM) of N-methoxyacetyl lyso $GM_1$ sodium salt (prepared according to Example 7) are dissolved in 5 ml of N-methylpyrrolidone and to this are added 44.5 µl (0.72 mM) of methyl iodide.

It is left to react for 3 hrs at room temperature, precipitated in ethyl acetate, filtered and vacuum dried.

The product is then purified by silica gel chromatography, using as eluent a mixture of chloroform/methanol/water (60:30:6).

The pure fractions are reunited, evaporated, re-dissolved in 2.5 ml of chloroform/methanol 1:1 and precipitated in 25 ml of acetone.

Product obtained: 457 mg (74% theoretical).

Silica gel chromatography, using as solvent a mixture of chloroform/methanol/CaCl$_2$ 0.3% (50:42:11), shows the product to be a unitary compound with Rf=0.4 (N-methoxyacetyl lyso GM$_1$=0.36).

EXAMPLE 20

Inner Ester of N-methoxyacetyl Lyso GM$_1$ 500 mg (0.36 mM) of N-methoxyacetyl lyso GM$_1$ sodium salt (prepared according to Example 7) are dissolved in 5 ml of N-methylpyrrolidone at 4° C. and reacted with 55 µl (0.4 mM) of triethylamine and 100 mg (0.41 mM) of 1-methyl-2-chloropyridine iodide.

Reaction is conducted for 4 hrs with a quantitative yield. The product is precipitated by adding 50 ml of acetone, then filtered and gathered with 5 ml of chloroform/isopropyl 1:1 and then reprecipitated in 25 ml of acetone.

Product obtained: 483 mg (98% theoretical).

Silica gel chromatography, using as solvent a mixture of chloroform/methanol/CaCl$_2$ 0.3% (50:42:11), shows the product to be a unitary compound with Rf=0.43 (N-methoxyacetyl lyso GM$_1$=0.36).

EXAMPLE 21

2-Butylamide of N-methoxyacetyl Lyso GM$_1$ 500 mg (0.36 mM) of the methyl ester of N-methoxyacetyl lyso GM$_1$ are dissolved in 5 ml of pyridine and to this are added 2.5 ml of 2-butylamine. It is left to react for 72 hrs at room temperature, after which it is dried in a rotary evaporator, gathered with 5 ml of chloroform/methanol 1:1 and precipitated in 25 ml of acetone, then filtered and vacuum dried.

The product is then purified by silica gel chromatography, using as eluent a mixture of chloroform/methanol/water (60:25:4).

The pure fractions are reunited, gathered, redissolved in 2.5 ml of chloroform/methanol 1:1 and precipitated in 25 ml of acetone.

Product obtained: 371 mg (72% theoretical).

Silica gel chromatography, using as solvent a mixture of chloroform/methanol/CaCl$_2$ 0.3% (50:42:11), shows the product to be a unitary compound with Rf=0.48 (methyl ester of N-methoxyacetyl lyso GM$_1$=0.4).

EXAMPLE 22

Peracetylate of the Methyl Ester of Methoxyacetyl Lyso GM$_1$ 500 mg (0.36 mM) of the methyl ester of N-methoxyacetyl lyso GM$_1$ are dissolved in 5 ml of pyridine and to this are added 2.5 ml of freshly distilled acetic anhydride and the mixture is kept under agitation for 72 hrs at room temperature. Once reaction is complete, the solution is evaporated by rotation and the residue divided between 10 ml of ice-cold water and 10 ml of ethyl acetate; the ethyl acetate is washed in cold HCl 1M, with water and a solution of Na$_2$Co$_3$ 1M. The organic phases are anhydrated with sodium sulfate, evaporated and the residue purified by silica gel chromatography, using a mixture of chloromethane/ethyl acetate/isopropanol (70:30:45).

The pure fractions are reunited, gathered, redissolved in 5 ml of ethyl ester and precipitated in 25 ml of n-hexane.

Product obtained: 450 mg (61% theoretical).

Silica gel chromatography, using as solvent a mixture of chloroform/methanol/ethyla cetate (70:10:30), and the acetate of ethyl/isopropanol (95:5), shows the product to be unitary with Rf of 0.45 and 0.26 respectively.

EXAMPLE 23

Inner Esters of N-dichloroacetyl Derivatives of a Mixture of Lysogangliosides 500 mg (0.29 mM) of the N-dichloroacetyl derivatives of a mixture of lysogangliosides, sodium salt (Example 18), are dissolved in 5 ml of N-methylpyrrolidone at 4° C. and reacted with 44.5 µl (0.32 mM) of triethylamine and 82.2 mg (0.32) of 1-methyl-2-chloropyridine iodide. Reaction is conducted for 4 hrs at 4° C. with a quantitative yield. The product is precipitated, adding 50 ml of acetone, filtered, gathered with 5 ml of dichloromethane/isopropanol 1:1 and then reprecipitated in 25 ml of acetone.

Product obtained: 457 mg.

The presence of inner esters is confirmed by infrared spectroscopy and thin layer chromatography. IR spectroscopy, effected with KBr pellets, showed a typical ester band at 1750 cm–1.

Silica gel chromatography using a solvent containing chloroform/methanol/CaCl$_2$ 0.3% (50:42:11), shows the product to have Rf of 0.43–0.60. The Rf of the products obtained is higher than that (<0.35) of the mixture of the starting compounds.

Chromatography therefore demonstrates a total absence of initial product. Treatment with a solution of 0.1N Na$_2$CO$_3$ at 60° for 1 hr, causes the ester bonds to be hydrolysed, thus obtaining an original mixture of ganglioside derivatives.

EXAMPLE 24

Methyl Esters of N-dichloroacetyl Derivatives of a Mixture of Lysogangliosides 500 mg (0.30 mM) of a mixture of inner esters of N-dichloroacetyl derivatives of a mixture of lysogangliosides, prepared as in Example 23, are dissolved in 20 ml of an anhydrous mixture of methylene and methanol chloride 4:1.

To this solution are added 32.4 mg (0.60 mM) of sodium methylate dissolved in 5 ml of anhydrous methanol and the mixture is left to reflux for 2 hrs. Once reaction is complete the mixture is neutralised with DOWEX AG 50x8 anhydrous resin (H+ form), the resin is separated by filtration and washed with methanol and the solution evaporated until dry. The residue is gathered in 5 ml methylene/methanol chloride 1:1 and the product of the reaction is precipitated by pouring it into 25 ml of acetone.

The raw product is then purified by chromatography on Sephadex-DEAE acetate form A-25, using as solvent a mixture of chloroform/methanol/water 30:60:8.

The neutral fractions are gathered, evaporated, dialyzed in water and evaporated again until dry. The residue is dissolved in 15 ml of chloroform/methanol 1:1 and the product precipitated with 75 ml of acetone. Yield 430 mg.

IR spectroscopy, effected on KBr pellets, shows a typical ester bond at 1750 cm–1.

Silica gel chromatography using as solvent a mixture of chloroform/methanol/CaCl$_2$ 0.3% (50:42:11), shows the product representing the mixture of methyl esters of N-dichloroacetyl derivatives of lysogangliosides, to have an Rf of 0.40–0.54 (Rf of the mixture of ganglioside derivatives, sodium salts, <0.35).

Complete transesterification can be confirmed by determining the molecular proportion between the alkoxy groups and sialic groups which are obtained by quantitative headspace gas chromatography of the methyl alcohol which is released after treatment with a solution of 0.1N $Na_2CO_3$ at 60° for 1 hr, which causes the scission of all the ester bonds, and by Svennerholm's method for the determination of N-acetylneuraminic acid.

EXAMPLE 25

2-butylamides of N-dichloroacetyl Derivatives of a Mixture of Lysogangliosides 500 mg (0.30 mM) of a mixture of inner esters of N-dichloroacetyl derivatives of a mixture of lysogangliosides, prepared as in Example 23, are dissolved in 2.5 ml of anhydrous pyridine. To the solution is added 1.25 ml of 2-butylamine and the mixture is kept under agitation in anhydrous conditions for 24 hrs at 25° C.

Once reaction is complete the solvent is eliminated by evaporation and the residue gathered with 5 ml of chloroform/methanol 1:1 and precipitated with 25 ml of acetone.

The raw product thus obtained is treated with 10 ml of $Na_2CO_3$ 1% for 30 min at 25° to hydrolyze the residual ester groups, then dialyzed in water. The solution is vacuum dried and the residue purified by chromatography with Sephadex-DEAE A-25, acetate form, using as solvent a mixture of chloroform/methanol/water 30:60:8.

The neutral fractions are evaporated until dry, dialyzed, evaporated again, dissolved in 5 ml of chloroform/methanol 1:1 and the product precipitated with 25 ml of acetone. Yield 425 mg. The IR spectrum no longer presents the typical ester band at 1750 cm−1.

Silica gel chromatography, using as solvent a mixture of chloroform/methanol/$CaCl_2$ 0.3% (50:42:11) and determined with resorcinol reagent shows the product representing the mixture of the 2-butylamides of the N-dichloroacetyl derivatives of lysogangliosides, to have Rf of 0.48–0.71 (Rf of the mixture of ganglioside derivatives, sodium salts, <0.35).

EXAMPLE 26

Peracetylated Derivative of Methyl Esters of N-dichloroacetyl Derivatives of a Mixture of Lysogangliosides 500 mg (0.29 mM) of a mixture of methyl esters of N-dichloroacetyl derivatives of a mixture of lysogangliosides (prepared as in Example 24), are dissolved in 5 ml of pyridine and to this are added 2.5 ml of freshly distilled acetic anhydride and the mixture is kept under agitation for 72 hrs at room temperature. Once reaction is complete, the solution is evaporated by rotation and the residue divided between 10 ml of ice-cold water and 10 ml of ethyl acetate. The ethyl acetate is washed with cold HCl 1M, with water and with a solution of $NaHCO_3$ 1M. The organic phases are anhydrated with sodium sulfate, evaporated and the residue purified by silica gel chromatography, using a mixture of dichloromethane/ethyl acetate/isopropanol 70:30:45.

The pure fractions are reunited, gathered, redissolved in 5 ml of ethyl ether and precipitated in 25 ml of n-hexane.

Product obtained: 485 mg.

Silica gel chromatography, using as solvent a mixture of chloroform/methanol/ethyl acetate 70:10:30, and the acetate of ethyl/isopropanol 95:5, shows the product to have Rf 0.23–0.54 and 0.01–0.52, respectively.

EXAMPLE 27

N-(3, 3-DICHLOROPIVALOYL)-LYSO GM1

500 mg (0.38 mM) of lyso GM1 are dissolved in 2.5 ml of dimethylformamide and to this are added 528 μl (3.8 mM) of triethylamine, 650 mg (3.8 mM) of 3,3-dichloropivalic acid and 194.2 mg (0.76 mM) of chloromethylpyridine iodide dissolved in 2.5 ml of dimethylformamide. It is left to react for 18 hours at room temperature and is then precipitated in 50 ml of ethyl acetate saturated with water. The product is dried and then purified by silica gel chromatography, eluting with a mixture of chloroform/methanol/water 60:35:8.

The pure fractions are pooled, evaporated, then gathered with $Na_2CO_3$ 1N, dialyzed against distilled water and then concentrated to 5 ml and precipitated in 50 ml of acetone. Product obtained: 365 mg (84% theoretical).

Silica gel chromatography using a solvent formed by chloroform/methanol/$CaCl_2$ 0.3% 50:42:11 shows a unitary compound with Rf=0.36.

EXAMPLE 28

N-(THREONYL)-LYSO GM1

500 mg (0.38 mM) of lyso GM1 are dissolved in 2.5 ml of dimethylformamide, and 528 μl (3.8 mM) of triethylamine, 648 mg (1.9 mM) of FMOC-threonine and 194.2 mg (0.76 mM) of chloromethylpyridine iodide dissolved in 2.5 ml of dimethylformamide are added at room temperature. It is left to react for 18 hours at room temperature, and then 2 ml of piperidine is added to remove the protective group (FMOC). It is again left to react for 3 hours at room temperature, and then precipitated in 100 ml of acetone. The product is filtered and dried. The resulting product is then purified by silica gel chromatography, eluting with a mixture of chloroform/methanol/water 60:35:8.

The pure fractions are pooled, evaporated, then gathered with $Na_2CO_3$ 1N, dialyzed against distilled water and then concentrated to 5 ml and precipitated in 50 ml of acetone. Product obtained: 323 mg (60% theoretical).

Silica gel chromatography using a solvent formed by chloroform/methanol/$CaCl_2$ 0.3% 50:42:11 shows a unitary compound with Rf=0.29.

EXAMPLE 29

N-(DIMETHYLGLYCYL)-LYSO GM1

500 mg (0.38 mM) of lyso GM1 are dissolved in 2.5 ml of dimethylformamide, and 528 μl (3.8 mM) of triethylamine, 196 mg (1.9 mM) of dimethylglycine and 194.2 mg (0.76 mM) of chloromethylpyridine iodide dissolved in 2.5 ml of dimethylformamide are added at room temperature. It is left to react for 18 hours at room temperature and then precipitated in 100 ml of acetone. The product is filtered and dried. The resulting product is then purified by silica gel chromatography, eluting with a mixture of chloroform/methanol/water 60:35:8.

The pure fractions are pooled, evaporated, then gathered with $Na_2CO_3$ 1N, dialyzed against distilled water and then concentrated to 5 ml and precipitated in 50 ml of acetone. Product obtained: 309 mg (58% theoretical).

Silica gel chromatography using a solvent-formed by chloroform/methanol/CaCl$_2$ 0.3% 50:42:11 shows a unitary compound with Rf=0.11.

EXAMPLE 30

N-(GLUTARYL)-LYSO GM1

500 mg (0.38 mM) of lyso GM1 are dissolved in 1 ml of dimethylformamide/methanol 1:1, and 161 μl (1.14 mM) of triethylamine and 130 μl (1.14 mM) of glutaric anhydride are added at 0° C. It is left to react at room temperature for 72 hours and then precipitated in 20 volumes of ethyl acetate, filtered and dried.

The product is then purified by silica gel chromatography, eluting with a mixture of chloroform/methanol/water 60:35:8.

The pure fractions are pooled, evaporated, then gathered with Na$_2$CO$_3$ 1N, dialyzed against distilled water and then concentrated to 5 ml and precipitated in 50 ml of acetone. Product obtained: 217 mg (40.0% theoretical).

Silica gel chromatography using a solvent formed by chloroform/methanol/CaCl$_2$ 0.2% 50:42:11, shows a unitary compound with Rf=0.30.

EXAMPLE 31

N-(CHLORODIFLUOROACETYL)-LYSO GM1

500 mg (0.38 mM) of lyso GM1 are dissolved in 2.5 ml of dimethylformamide/methanol 1:1, and 528 μl (3.8 mM) of triethylamine and 277 mg (1.14 mM) of chlorodifluoroacetic anhydride are added at 0° C. It is left to react at room temperature for 72 hours, precipitated in 20 volumes of ethyl acetate, filtered and dried.

The product is then purified by silica gel chromatography, eluting with a mixture of chloroform/methanol/water 60:35:8.

The pure fractions are pooled, evaporated, then gathered with Na$_2$CO$_3$ 1N, dialyzed against distilled water and then concentrated to 5 ml and precipitated in 50 ml of acetone. Product obtained: 333 mg (62.0% theoretical).

Silica gel chromatography using a solvent formed by chloroform/methanol/CaCl$_2$ 0.2% 50:42:11, shows a unitary compound with Rf=0.37.

EXAMPLE 32

N-(ISOLEUCYL)-LYSO GM1

500 mg (0.38 mM) of lyso GM1 are dissolved in 2.5 ml of dimethylformamide, and 528 μl (3.8 mM) of triethylamine, 671 mg (1.9 mM) of FMOC-isoleucine and 194.2 mg (0.76 mM) of chloromethylpyridine iodide dissolved in 2.5 ml of dimethylformamide are added at room temperature. It is left to react for 18 hours at room temperature, and then 2 ml of piperidine is added to remove the protective group (FMOC). It is again left to react for 3 hours at room temperature, precipitated in 100 ml of acetone, filtered and dried. The product is then purified by silica gel chromatography, eluting with a mixture of chloroform/methanol/water 60:35:8.

The pure fractions are pooled, evaporated, then gathered with Na$_2$CO$_3$ 1N, dialyzed against distilled water and then concentrated to 5 ml and precipitated in 50 ml of acetone. Product obtained: 298 mg (55% theoretical).

Silica gel chromatography using a solvent formed by chloroform/methanol/CaCl$_2$ 0.3% 50:42:11 shows a unitary compound with Rf=0.28.

EXAMPLE 33

Pharmaceutical Preparations in Solution for Injection

Preparation No.1—one 2 ml vial contains:

| | |
|---|---|
| active substance | mg 5 |
| sodium chloride | mg 16 |
| citrate buffer pH 6 in | |
| distilled water to a vol. of ml 2 | |

The active substance is chosen from the group constituted by the ganglioside derivatives described in any one of Examples 3, 4 and 18.

Preparation No.2—one 2 ml vial contains:

| | |
|---|---|
| active substance | mg 50 |
| sodium chloride | mg 16 |
| citrate buffer pH 6 in | |
| distilled water to a vol. of ml 2 | |

The active substance is chosen from the group constituted by the ganglioside derivatives described in any one of Examples 5, 6 and 7.

Preparation No.3—one 4 ml flacon contains:

| | |
|---|---|
| active substance | mg 100 |
| sodium chloride | mg 32 |
| citrate buffer pH 6 in | |
| distilled water to a vol. of ml 4 | |

The active substance is chosen from the group constituted by the ganglioside derivatives described in any one of Examples 9, 10 and 14.

Preparations Nos. 1, 2 and 3 can be directly administered to animals or humans by any one of the described routes. Furthermore, the formulations can contain a pharmaceutically active substance.

EXAMPLE 34

Pharmaceutical Compositions Prepared in Double Flacons

The preparations illustrated in this Example are prepared in double flacons. The first flacon contains the active substance in the form of a freeze-dried powder in a quantity which may vary between 10% and 90% in weight, together with a pharmaceutically acceptable excipient, with glycine or mannitol. The second flacon contains the solvent, as a solution of sodium chloride and a citrate buffer. The contents of the two flacons are mixed immediately before use and the powder of the freeze-dried active substance rapidly dissolves to form an injectable solution. The pharmaceutical form represented by a flacon containing the freeze-dried powder of the active substance, is the preferred form of the present invention.

System No.1
a. one 2 ml vial of freeze-dried substance contains:

| active substance | mg 5 |
|---|---|
| glycine | mg 30 | b. one 2 ml vial of solvent contains:

| sodium chloride | mg 16 |
|---|---|
| citrate buffer in distilled water to | ml 2 |

The active substance is chosen from the group constituted by the ganglioside derivatives described in any one of Examples 19, 20 and 22.

System No.2
a. one 3 ml vial of freeze-dried substance contains:

| active substance | mg 5 |
|---|---|
| mannitol | mg 40 | b. one 2 ml vial of solvent contains:

| sodium chloride | mg 16 |
|---|---|
| citrate buffer in distilled water to | ml 2 |

The active substance is chosen from the group constituted by the ganglioside derivatives described in either one of Examples 23 and 24.

System No.3
a. one 3 ml vial of freeze-dried substance contains:

| active substance | mg 50 |
|---|---|
| glycine | mg 25 | b. one 3 ml vial of solvent contains:

| sodium chloride | mg 24 |
|---|---|
| citrate buffer in distilled water to | ml 3 |

The active substance is chosen from the group constituted by the ganglioside derivatives described in Example 26.

System No.4
a. one 3 ml vial of freeze-dried substance contains:

| active substance | mg 50 |
|---|---|
| mannitol | mg 20 | b. one 3 ml vial of solvent contains:

| sodium chloride | mg 24 |
|---|---|
| citrate buffer in distilled water to | ml 3 |

The active substance is chosen from the group constituted by the ganglioside derivatives described in Example 26.

System No.5
a. one 5 ml flacon of freeze-dried substance contains:

| active substance | mg 150 |
|---|---|
| glycine | mg 50 | b. one 4 ml vial of solvent contains:

| sodium chloride | mg 32 |
|---|---|
| citrate buffer in distilled water to | ml 4 |

The active substance is chosen from the group constituted by the ganglioside derivatives described in either one of Examples 23 and 24.

System No.6
a. one 5 ml flacon of freeze-dried substance contains:

| active substance | mg 100 |
|---|---|
| mannitol | mg 40 | b. one 4 ml vial of solvent contains:

| sodium chloride | mg 32 |
|---|---|
| citrate buffer in distilled water to | ml 4 |

The active substance is chosen from the group constituted by the ganglioside derivatives described in any one of Examples 23, 24 and 26.

What is claimed is:

1. A pharmaceutical composition containing, as active ingredient, an N-acyl-lysoganglioside wherein the acyl group is derived from an aliphatic acid having from 2 to 12 carbon atoms, substituted with at least one polar group selected from the group consisting of chlorine and fluorine and etherified hydroxy groups or esters or amides of the sialic carboxy groups of said N-acyl-lysogangliosides, inner esters of said N-acyl-lysogangliosides, peracylated derivatives of said N-acyl-lysogangliosides, metal salts or organic base salts of said N-acyl-lysogangliosides having acid groups, acid addition salts of said N-acyl-lysogangliosides and mixtures of said N-acyl-lysogangliosides, together with a pharmaceutically acceptable excipient.

2. The pharmaceutical composition according to claim 1, wherein the active ingredient is N-monochloroacetyl-lyso $GM_1$.

3. The pharmaceutical composition according to claim 1, wherein the active ingredient is N-dichloroacetyl-lyso $GM_1$.

* * * * *